United States Patent [19]

Al-Razzak et al.

[11] Patent Number: 5,610,193
[45] Date of Patent: Mar. 11, 1997

[54] PHARMACEUTICAL COMPOSITION

[75] Inventors: Laman A. Al-Razzak, Libertyville; Kennan C. Marsh, Lake Forest; Richard A. Pyter, Libertyville, all of Ill.

[73] Assignee: Abbott Laboratories, Abbott Park, Ill.

[21] Appl. No.: 650,261

[22] Filed: May 22, 1996

Related U.S. Application Data

[60] Continuation of Ser. No. 424,740, Apr. 18, 1995, abandoned, which is a division of Ser. No. 297,004, Aug. 31, 1994, Pat. No. 5,559,158, which is a continuation-in-part of Ser. No. 267,273, Jun. 28, 1994, abandoned, which is a continuation-in-part of Ser. No. 130,409, Oct. 1, 1993, abandoned.

[51] Int. Cl.⁶ .................. A61K 31/16; A61K 31/695; A61K 31/425; A61K 9/48
[52] U.S. Cl. ............... 514/616; 514/63; 514/365; 514/374; 514/962; 424/451; 424/484
[58] Field of Search ................... 424/451, 484; 514/63, 365, 374, 616, 962

[56] References Cited

U.S. PATENT DOCUMENTS 5,206,219  4/1993  Desai .................................. 514/3

FOREIGN PATENT DOCUMENTS

| | | |
|---|---|---|
| 486948 | 5/1992 | European Pat. Off. . |
| 490667 | 6/1992 | European Pat. Off. . |
| 532466 | 3/1993 | European Pat. Off. . |
| 541168 | 5/1993 | European Pat. Off. . |
| WO92/08701 | 5/1992 | WIPO . |
| WO93/07128 | 4/1993 | WIPO . |
| WO94/05639 | 3/1994 | WIPO . |
| WO94/14436 | 7/1994 | WIPO . |

*Primary Examiner*—Kevin E. Weddington
*Attorney, Agent, or Firm*—Steven R. Crowley

[57] ABSTRACT

A solid pharmaceutical composition is disclosed which comprises a pharmaceutically acceptable adsorbent or a mixture of pharmaceutically acceptable adsorbents to which is adsorbed a mixture of (1) a pharmaceutically acceptable organic solvent or a mixture of pharmaceutically acceptable organic solvents, (2) an HIV protease inhibiting compound and (3) one or more pharmaceutically acceptable acids. The solid composition can optionally be encapsulated in a hard gelatin capsule.

3 Claims, No Drawings

PHARMACEUTICAL COMPOSITION

This is a continuation of U.S. patent application Ser. No. 08/424,740 filed Apr. 18, 1995 now abandoned, which is a division of U.S. patent application Ser. No. 08/297,004, filed Aug. 31, 1994, which is now U.S. Pat. No. 5,559,158, which is a continuation-in-part of U.S. patent application Ser. No. 267,273, filed Jun. 28, 1994, now abandoned, which is a continuation-in-part of U.S. patent application Ser. No. 130,409, filed Oct. 1, 1993, now abandoned.

TECHNICAL FIELD

A solid pharmaceutical composition providing improved oral bioavailability is disclosed for compounds which are inhibitors of HIV protease (in particular, HIV-1 and HIV-2 protease). In particular, the composition comprises a pharmaceutically acceptable adsorbent or a mixture of pharmaceutically acceptable adsorbents to which is adsorbed a mixture of (1) a pharmaceutically acceptable organic solvent or a mixture of pharmaceutically acceptable organic solvents, (2) an HIV protease inhibitor and (3) a pharmaceutically acceptable acid. The solid composition can be encapsulated in a hard gelatin capsule.

BACKGROUND OF THE INVENTION

One measure of the potential usefulness of an oral dosage form of a new pharmaceutical agent is the bioavailability observed after oral administration of the dosage form. Various factors can affect the bioavailability of a drug when administered orally. These factors include aqueous solubility, drug absorption throughout the gastrointestinal tract, dosage strength and first pass effect. Aqueous solubility is one of the most important of these factors. When a drug has poor aqueous solubility, attempts are often made to identify salts or other derivatives of the drug which have improved aqueous solubility. When suitable aqueous solubility for a drug (or its salt or other derivative) is not obtainable, it is generally true that a solid composition, for example, a tablet or capsule comprising the drug (or its salt or other derivative), will not provide acceptable oral bioavailability.

It has recently been determined that HIV protease inhibiting compounds are useful for inhibiting HIV protease in vitro and in vivo, are useful for inhibiting HIV (human immunodeficiency virus) infections and are useful for treating AIDS (acquired immunodeficiency syndrome). HIV protease inhibiting compounds typically are characterized by having poor oral bioavailability.

Examples of HIV protease inhibiting compounds include N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide and related compounds, disclosed in European Patent Application No. EP541168, published May 12, 1993;

N-tert-butyl-decahydro-2-[2(R)-hydroxy-4-phenyl-3(S)-[[N-(2-quinolylcarbonyl)-L-asparainyl ]amino]butyl]-(4aS,8aS)-isoquinoline-3(S)-carboxamide (i.e., saquinavir) and related compounds, disclosed in U.S. Pat. No. 5,196,438, issued Mar. 23, 1993;

5(S)-Boc-amino-4(S)-hydroxy-6-phenyl-2(R)-phenylmethylhexanoyl-(L)-Val-(L)-Phe-morpholin-4-ylamide and related compounds, disclosed in European Patent Application No. EP532466, published Mar. 17, 1993;

1-Naphthoxyacetyl-beta-methylthio-Ala-(2S,3S )-3-amino-2-hydroxy-4-butanoyl1,3-thiazolidine-4-t-butylamide (i.e., 1-Naphthoxyacetyl-Mta-(2S,3S)-AHPBA-Thz-NH-tBu) and related compounds, disclosed in European Patent Application No. EP490667, published Jun. 17, 1992;

[1S-[1R*(R*), 2S*]]-$N^1$[3-[[[(1,1-dimethylethyl)amino]carbonyl](2-methylpropyl)amino]-2-hydroxy-1-(phenylmethyl)propyl]-2-[(2-quinolinylcarbonyl) amino]-butanediamide and related compounds, disclosed in PCT Patent Application No. WO92/08701, published May 29, 1992;

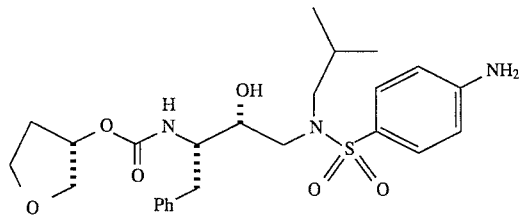

and related compounds, disclosed in PCT Patent Application No. WO94/05639, published Mar. 17, 1994; and

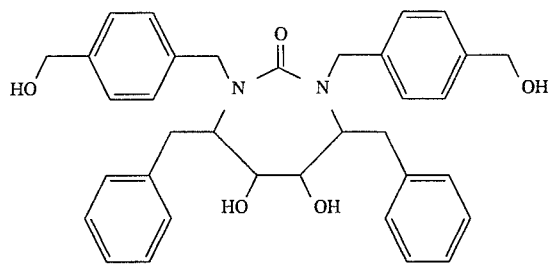

and related compounds, disclosed in PCT Patent Application No. WO93/07128, published Apr. 15, 1993.

It has recently been determined that compounds of the formula I:

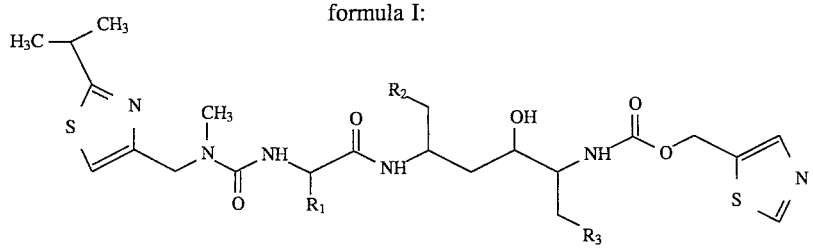

I wherein $R_1$ is lower alkyl and $R_2$ and $R_3$ are phenyl are inhibitors of HIV-1 and HIV-2 protease and are useful to inhibit HIV infections and, thus, are useful for the treatment of AIDS.

In particular, the compound of formula II, has been found to be especially effective as an inhibitor of HIV-1 and HIV-2 protease.

II

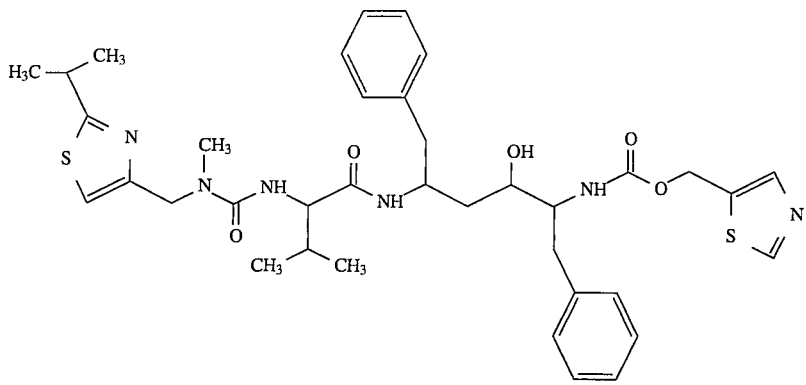

The most preferred compound of formula II is (2S,3S, 5S)-5-(N-(N-((N-Methy-N-( 2-isopropyl-4-thiazolyl)methyl)-amino)carbonyl)valinyl) amino)-2-(N-((5-thiazolyl) methoxycarbonyl)amino)- 1,6-diphenyl-3-hydroxyhexane (compound III).

Compound III has an aqueous solubility of approximately 6 micrograms per milliliter at pH >2. Acid addition salts of compound III (for example, bis-hydrochloride, bis-tosylate, bis-methane sulfonate and the like) have aqueous solubilities of <0.1 milligram/milliliter. Therefore, it is not surprising that when compound III or a salt thereof is administered orally to dogs, the bioavailability is less than 2%.

The oral bioavailability of a compound having poor aqueous solubility can sometimes be improved by administering the compound as a polyethylene glycol (PEG) melt (solid dispersion). The bioavailability in dogs of such a composition comprising compound III is <5%.

The oral bioavailability of a compound having poor aqueous solubility can also sometimes be improved by including in a standard solid composition a surfactant (for example, sodium lauryl sulfate) and a pharmaceutically acceptable acid. The bioavailability in dogs of such a composition comprising compound III is <3%.

In order to have a suitable oral dosage form of compound III, the oral bioavailability of compound III should be at least about 25%. Preferably, the oral bioavailability of compound III from the dosage form should be greater than about 40% and, more preferably, greater than about 50%.

It has been found that compound III has good solubility in pharmaceutically acceptable organic solvents and that the solubility in such solvents is enhanced in the presence of a pharmaceutically acceptable acid. However, it does not necessarily follow that oral administration of a composition comprising such an organic solution of compound III would provide good bioavailability. Unexpectedly, when a mixture of compound III and one or more pharmaceutically acceptable organic solvents is adsorbed on a pharmaceutically acceptable adsorbent and this composition is administered to dogs, an oral bioavailability as high as about 90% is observed.

DISCLOSURE OF THE INVENTION

In accordance with the present invention, there is a solid pharmaceutical composition comprising a pharmaceutically acceptable adsorbent or a mixture of pharmaceutically acceptable adsorbents to which is adsorbed a mixture of (1) a pharmaceutically acceptable organic solvent or a mixture of pharmaceutically acceptable organic solvents, (2) an HIV protease inhibiting compound (preferably, a compound of the formula II) and (3) a pharmaceutically acceptable acid or a combination of pharmaceutically acceptable acids.

Also in accordance with the present invention, there is a solid pharmaceutical composition comprising a pharmaceutically acceptable adsorbent or a mixture of two or more pharmaceutically acceptable adsorbents to which is adsorbed a mixture of (1) a pharmaceutically acceptable organic solvent or a mixture of two or more pharmaceutically acceptable organic solvents, (2) an HIV protease inhibiting compound (preferably, a compound of the formula II) and (3) a pharmaceutically acceptable acid or a combination of pharmaceutically acceptable acids, wherein the solid composition is encapsulated in a hard gelatin capsule.

Preferably, the adsorbed mixture is in the form of a solution. The adsorbed mixture can also comprise one or more additives, including one or more pharmaceutically acceptable oils. The adsorbed mixture of the invention can also comprise one or more pharmaceutically acceptable surfactants. The adsorbed mixture of the invention can also comprise antioxidants (for example, ascorbic acid, BHA (butylated hydroxyanisole), BHT (butylated hydroxytoluene), vitamin E, vitamin E PEG 1000 succinate and the like).

The solid composition of this invention provides improved oral bioavailability for compound II when compared to non-formulated compound II (base) or non-formulated compound II (acid addition salt). The solid composition of this invention also provides improved oral bioavailability for compound II when compared to a PEG melt composition or a standard solid composition which also contains a surfactant and a pharmaceutically acceptable acid.

The term "pharmaceutically acceptable adsorbent" as used herein refers to silicon dioxide, colloidal silicon dioxide (for example, Cab-o-sil®, available from Cabot Corp.), microcrystalline cellulose, starch, maltodextrin, talc, calcium carbonate, pectin, aluminum silicate, crospovidone (for example, Polyplasdone®XL or XL10, available from GAF Corp.) and the like.

The term "pharmaceutically acceptable organic solvent" as used herein refers to propylene glycol; polypropylene glycol; polyethylene glycol (for example, polyethylene glycol 300, polyethylene glycol 400, polyethylene glycol 600, polyethylene glycol 900, polyethylene glycol 540 (all available from Union Carbide) and the like); polyoxyethylene castor oil derivatives (for example, polyoxyethyleneglycerol triricinoleate or polyoxyl 35 castor oil (Cremophor®EL, BASF Corp.), polyoxyethyleneglycerol oxystearate (Cremophor®RH 40 (polyethyleneglycol 40 hydrogenated castor oil) or Cremophor®RH 60 (polyethyleneglycol 60 hydrogenated castor oil), BASF Corp.) and the like); ethanol; 2-(2-ethoxyethoxy)ethanol (Transcutol®, Gattefosse, Westwood, N.J. 07675); benzyl alcohol; glycerol; ethyl oleate, isopropyl palmitate, isopropyl myristate and the like; N-methylpyrrolidinone; pharmaceutically acceptable silicon fluids; and the like.

The term "pharmaceutically acceptable acid" as used herein refers to (i) an inorganic acid such as hydrochloric acid, hydrobromic acid, hydroiodic acid and the like, (ii) an organic mono-, di- or tri-carboxylic acid (for example, formic acid, acetic acid, adipic acid, alginic acid, citric acid, ascorbic acid, aspartic acid, benzoic acid, butyric acid, camphoric acid, gluconic acid, glucuronic acid, galactaronic acid, glutamic acid, heptanoic acid, hexanoic acid, fumaric acid, lactic acid, lactobionic acid, malonic acid, maleic acid, nicotinic acid, oxalic acid, pamoic acid, pectinic acid, 3-phenylpropionic acid, picric acid, pivalic acid, propionic acid, succinic acid, tartaric acid, undecanoic acid and the like) or (iii) a sulfonic acid (for example, benzenesulfonic acid, sodium bisulfate, sulfuric acid, camphorsulfonic acid, dodecylsulfonic acid, ethanesulfonic acid, methanesulfonic acid, isethionic acid, naphthalenesulfonic acid, p-toluenesulfonic acid and the like).

The term "pharmaceutically acceptable oil" as used herein refers to mineral oil or a vegetable oil (for example, safflower oil, peanut oil, olive oil, fractionated coconut oil (for example, mixed triglycerides with caprylic acid and capric acid (Miglyol® 81 2, available from Huls AG, Witten, Germany) and the like), propyleneglycol monolaurate and the like.

The term "pharmaceutically acceptable surfactant" as used herein refers to a pharmaceutically acceptable non-ionic surfactant (for example, polyoxyethylenepolypropylene glycol, such as Poloxamer® 68 (BASF Wyandotte Corp.) or a mono fatty acid ester of polyoxyethylene (20) sorbitan (for example, polyoxyethylene (20) sorbitan monooleate or polysorbate 80 (Tween®80), polyoxyethylene (20) sorbitan monostearate or polysorbate 60 (Tween®60), polyoxyethylene (20) sorbitan monopalmitate or polysorbate 40 (Tween®40), polyoxyethylene (20) sorbitan monolaurate or polysorbate 20 (Tween®20) and the like) and the like) or a pharmaceutically acceptable anionic surfactant (for example, sodium lauryl sulfate or bile salts (for example, sodium cholate, sodium deoxycholate and the like) and the like).

A preferred composition of the invention comprises a solid pharmaceutical composition comprising a pharmaceutically acceptable adsorbent or a mixture of pharmaceutically acceptable adsorbents to which is adsorbed a mixture of (1) a pharmaceutically acceptable organic solvent or a mixture of pharmaceutically acceptable organic solvents, (2) an HIV protease inhibiting compound (prefereably, a compound of the formula II) in the amount of from about 10% to about 40% by weight of the solid composition and (3) a total of from about 0.2 molar equivalent to about 2 molar equivalents (based on the HIV protease inhibiting compound) of (a) a pharmaceutically acceptable acid or (b) a combination of pharmaceutically acceptable acids.

Preferably, the pharmaceutically acceptable adsorbent or mixture of pharmaceutically acceptable adsorbents comprises from about 25% to about 75% by weight of the solid pharmaceutical composition. More preferably, the pharmaceutically acceptable adsorbent or mixture of pharmaceutically acceptable adsorbents comprises from about 25% to about 45% by weight of the solid pharmaceutical composition.

A preferred pharmaceutically acceptable adsorbent is silicon dioxide (from about 25% to about 50% by weight of the solid pharmaceutical composition) or a mixture of silicon dioxide (from about 15% to about 35% by weight of the solid pharmaceutical composition) and an adsorbent or a mixture of adsorbents independently selected from talc (from about 1% to about 5% by weight of the solid pharmaceutical composition), corn starch (from about 5% to about 10% by weight of the solid pharmaceutical composition), microcrystalline cellulose (from about 5% to about 20% by weight of the solid pharmaceutical composition) and maltodextrin (from about 5% to about 10% by weight of the solid pharmaceutical composition).

Preferably, the pharmaceutically acceptable organic solvent or mixture of pharmaceutically acceptable organic solvents comprises from about 10% to about 60% by weight of the solid pharmaceutical composition. More preferably, the pharmaceutically acceptable organic solvent or mixture of pharmaceutically acceptable organic solvents comprises from about 20% to about 55% by weight of the solid pharmaceutical composition.

A preferred pharmaceutically acceptable organic solvent comprises propylene glycol (from about 10% to about 45% by weight of the solid pharmaceutical composition) or a mixture of propylene glycol (from about 10% to about 20% by weight of the solid pharmaceutical composition) and Cremephor® EL (from about 4% to about 12% by weight of the solid pharmaceutical composition) or a mixture of propylene glycol (from about 10% to about 20% by weight of the solid pharmaceutical composition) and Cremephor® EL (from about 4% to about 12% by weight of the solid pharmaceutical composition) and ethanol (from about 3% to about 25% by weight of the solid pharmaceutical composition, more preferably from about 20% to about 25% by weight of the solid pharmaceutical composition).

A preferred pharmaceutically acceptable acid is p-toluenesulfonic acid, citric acid or hydrochloric acid.

A more preferred composition of the invention comprises a solid pharmaceutical composition comprising a pharmaceutically acceptable adsorbent or a mixture of two or more pharmaceutically acceptable adsorbents to which is adsorbed a mixture of (1) a pharmaceutically acceptable organic solvent or a mixture of pharmaceutically acceptable organic solvents, (2) an HIV protease inhibiting compound (prefereably, a compound of the formula II) in the amount of from about 10% to about 40% by weight and (3) a total of from about 0.2 to about 1 molar equivalent (based on the HIV protease inhibiting compound) of (a) a pharmaceutically acceptable acid or (b) a combination of pharmaceutically acceptable acids, wherein the solid composition is encapsulated in a hard gelatin capsule.

In the more preferred composition of the invention, the more preferred pharmaceutically acceptable adsorbents, solvents and acids are as described above for the preferred composition of the invention.

A more highly preferred composition of the invention comprises a solid pharmaceutical composition comprising a pharmaceutically acceptable adsorbent comprising a mixture of about 25% by weight of the solid composition of silicon dioxide and from about 15% to about 20% by weight of the solid composition of microcrystalline cellulose to which mixture of adsorbents is adsorbed a mixture of (1) from about 15% to about 20% by weight of the solid composition of propylene glycol, (2) about 5% by weight of the solid composition of polyoxyethyleneglycerol triricinoleate, (3) from about 20% to about 25% by weight of the solid composition of a compound of formula II and (4) from about 0.2 to about 1 molar equivalent, based upon the amount of the compound of formula II, of hydrochloric acid.

A most preferred composition of the invention comprises a solid pharmaceutical composition comprising a pharmaceutically acceptable adsorbent or a mixture of pharmaceutically acceptable adsorbents to which is adsorbed a mixture of (1) a pharmaceutically acceptable organic solvent or a mixture of pharmaceutically acceptable organic solvents, (2) a compound of the formula III in the amount of from about 10% to about 40% by weight and (3) a total of from about 0.2 to about about 1 molar equivalent (based on compound III) of (a) a pharmaceutically acceptable acid or (b) a combination of pharmaceutically acceptable acids, wherein the solid composition is encapsulated in a hard gelatin capsule.

In the most preferred composition of the invention, the most preferred pharmaceutically acceptable adsorbents, solvents and acids are as described above for the preferred composition of the invention.

A most highly preferred composition of the invention comprises a solid pharmaceutical composition comprising a pharmaceutically acceptable adsorbent comprising a mixture of about 25% by weight of the solid composition of silicon dioxide and from about 15% to about 20% by weight of the solid composition of microcrystalline cellulose to which mixture of adsorbents is adsorbed a mixture of (1) from about 15% to about 20% by weight of the solid composition of propylene glycol, (2) about 5% by weight of the solid composition of polyoxyethyleneglycerol triricinoleate, (3) from about 20% to about 25% by weight of the solid composition of a compound of formula III and (4) from about 0.2 to about 1 molar equivalent, based upon the amount of the compound of formula III, of hydrochloric acid.

Another most highly preferred composition of the invention comprises a solid pharmaceutical composition comprising a pharmaceutically acceptable adsorbent comprising from about 25% to about 30% by weight of the solid composition of silicon dioxide to which adsorbent is adsorbed a mixture of (1) from about 10% to about 15% by weight of the solid composition of propylene glycol, (2) from about 4% to about 5% by weight of the solid composition of polyoxyethyleneglycerol triricinoleate, (3) from about 20% to about 25% by weight of the solid composition of ethanol, (4) from about 20% to about 25% by weight of the solid composition of a compound of formula III and (5) from about 0.2 to about 0.5 molar equivalents, based upon the amount of the compound of formula III, of hydrochloric acid.

Another most highly preferred composition of the invention comprises a solid pharmaceutical composition comprising a pharmaceutically acceptable adsorbent comprising from about 30% to about 35% by weight of the solid composition of silicon dioxide to which adsorbent is adsorbed a mixture of (1) from about 40% to about 45% by weight of the solid composition of propylene glycol, (2) from about 10% to about 20% by weight of the solid composition of a compound of formula III and (3) from about 0.2 to about 2 molar equivalents, based upon the amount of the compound of formula III, of p-toluenesulfonic acid.

Another most highly preferred composition of the invention comprises a solid pharmaceutical composition comprising a pharmaceutically acceptable adsorbent comprising a mixture of from about 25% to about 30% by weight of the solid composition of silicon dioxide, from about 10% to about 15% by weight of the solid composition of microcrystalline cellulose and about 5% by weight of the solid composition of talc to which adsorbent is adsorbed a mixture of (1) from about 35% to about 40% by weight of the solid composition of propylene glycol, (2) from about 10% to about 15% by weight of the solid composition of a compound of formula III and (5) from about 0.2 to about 2 molar equivalents, based upon the amount of the compound of formula III, of p-toluenesulfonic acid.

Another most highly preferred composition of the invention comprises a solid pharmaceutical composition comprising a pharmaceutically acceptable adsorbent comprising a mixture of from about 30% to about 35% by weight of the solid composition of silicon dioxide, from about 5% to about 10% by weight of the solid composition of microcrystalline cellulose and about 1% by weight of the solid composition of talc to which adsorbent is adsorbed a mixture of (1) from about 30% to about 35% by weight of the solid composition of propylene glycol, (2) from about 15% to about 20% by weight of the solid composition of a compound of formula III and (5) from about 0.2 to about 2 molar equivalents, based upon the amount of the compound of formula III, of p-toluenesulfonic acid.

The compounds of formula 1 and II contain two or more asymmetric carbon atoms and thus can exist as pure diastereomers, mixtures of diastereomers, diastereomeric racemates or mixtures of diastereomeric racemates. The present invention is intended to include within its scope all of the isomeric forms. The terms "R" and "S" configuration as used herein are as defined by IUPAC 1974 Recommendations for Section E, Fundamental Stereochemistry, Pure Appl. Chem.(1976) 45, 13–30.

The preferred isomer of the compound of formula II is (2S,3S,5S)-5-(N-(N-( (N-Methyl-N-((2-isopropyl-4-thiazolyl)methyl)-amino)carbonyl)-valinyl)amino )-2-(N-((5-thiazolyl)methoxycarbonyl)amino)-1,6-diphenyl-3-hydroxyhexane (compound III).

The term "lower alkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

Hard gelatin capsules are purchased from Capsugel, Greenwood, S.C. Capsules are filled manually or by capsule filling machine. The target filling weight depends on the potency of the filling composition in combination with the desired dosage strength.

The following examples will serve to further illustrate the invention. In particular, Examples 7–16 relate directly to the composition of the invention.

EXAMPLE 1 (non-formulated capsules)

An amount of compound III (free base) equivalent to a 5 mg/kg dose was placed in hard gelatin capsules (gray, size 0). These capsules were administered to fasted dogs with 10 mL of water.

EXAMPLE 2 (Capsule)

An amount of compound III (free base) equivalent to a 5 mg/kg dose was placed in hard gelatin capsules (gray, size 0). These capsules were administered to non-fasted dogs with 10 mL of water.

EXAMPLE 3 (Capsule)

An amount of the di-tosylate salt of compound III equivalent to a 5 mg/kg dose of compound III (base equivalent)

was filled into hard gelatin capsules (gray, size 0). These capsules were administered to fed dogs with 10 mL of water.

EXAMPLE 4 (Capsule, PEG Melt)

| Component | % By Weight |
| --- | --- |
| Compound III (free base) | 33.0 |
| Citric Acid, anhydrous, powder, USP | 8.3 |
| Malonic acid | 8.3 |
| Polyethylene Glycol 1450 | 50.0 |
| Lactose monohydrate NF, powder, regular | 0.4 |

EXAMPLE 5 (Capsule)

| Component | % By Weight |
| --- | --- |
| Compound III (free base) | 27.0 |
| Citric Acid, anhydrous, powder, USP | 21.0 |
| p-toluene sulfonic acid, monohydrate, Sigma | 20.0 |
| Microcrystalline cellulose PH101, NF | 15.0 |
| Lactose monohydrate NF, powder, regular | 11.0 |
| Hydroxypropyl cellulose, NF | 4.0 |
| Sodium Lauryl Sulfate, NF | 1.5 |
| Magnesium Stearate, NF impalpable powder | 0.5 |

EXAMPLE 6 (Tablet)

| Component | % By Weight |
| --- | --- |
| Compound III (free base) | 20.0 |
| Citric Acid, anhydrous, powder, USP | 12.0 |
| p-toluene sulfonic acid, monohydrate, Sigma | 12.0 |
| Microcrystalline cellulose PH101, NF | 20.0 |
| Lactose monohydrate NF, powder, regular | 12.5 |
| Sodium Lauryl Sulfate, NF | 1.5 |
| Sodium Alginate, Sigma high viscosity | 20.0 |
| Sodium Starch Glycolate | 2.0 |

In general, the compositions of this invention can be prepared in the following manner. The pharmaceutically acceptable acid or acids are added to the pharmaceutically acceptable organic solvent or mixture of solvents with mixing. Ethanol (dehydrated, USP, 200 proof) can be used as a cosolvent. If an antioxidant is used, it is then added with mixing. Then the HIV protease inhibitor is slowly added with mixing until it is completely dissolved. Lastly, any viscous pharmaceutically acceptable organic cosolvents and/or other additives, such as surfactants, are added with mixing.

The pharmaceutically acceptable adsorbent or mixture of adsorbents is charged into a Hobart mixer and mixed. The above solution is added dropwise to the dry mixture in the Hobart mixer while mixing at slow speed. The mixture is massed until granular.

The granulation is screened through an appropriate sized screen. If ethanol is used as a cosolvent, prior to being filled into capsules, the wet granulation can optionally be dried in a tray dryer or a fluidbed dryer until the loss on drying is not greater than the amount of ethanol originally in the adsorbed solution.

The final concentration of the HIV protease inhibitor (mg/g of granulation) in the granulation is determined by HPLC analysis. Capsules (gelatin, No. 00, iron gray opaque) are filled with the appropriate amount of the granulation to provide the desired dose of HIV protease inhibitor per capsule.

EXAMPLE 7 (capsule)

| Component | % By Weight |
| --- | --- |
| Wet Granulation Composition | |
| Compound III (free base) | 15.0 |
| Propylene glycol, USP | 42.7 |
| Ethanol, dehydrated USP, 200 proof | 4.0 |
| Silicon Dioxide, NF | 30.0 |
| p-toluene sulfonic acid, monohydrate, Sigma | 8.3 |
| Dry Granulation Composition | |
| Compound III (free base) | 15.6 |
| Propylene glycol, USP | 44.5 |
| Silicon Dioxide, NF | 31.3 |
| p-toluene sulfonic acid, monohydrate, Sigma | 8.6 |

EXAMPLE 8 (capsule)

| Component | % By Weight |
| --- | --- |
| Wet Granulation Composition | |
| Compound III (free base) | 15.0 |
| Propylene glycol, USP | 42.7 |
| Ethanol, dehydrated USP, 200 proof | 4.0 |
| Silicon Dioxide, NF | 20.0 |
| p-toluene sulfonic acid, monohydrate, Sigma | 8.3 |
| Talc | 5.0 |
| Corn Starch | 5.0 |
| Dry Granulation Composition | |
| Compound III (free base) | 15.6 |
| Propylene glycol, USP | 44.5 |
| Silicon Dioxide, NF | 20.8 |
| p-toluene sulfonic acid, monohydrate, Sigma | 8.6 |
| Talc | 5.2 |
| Corn Starch | 5.2 |

EXAMPLE 9 (capsule)

| Component | % By Weight |
| --- | --- |
| Wet Granulation Composition | |
| Compound III (free base) | 12.8 |
| Propylene glycol, USP | 36.6 |
| Ethanol, dehydrated USP, 200 proof | 3.4 |
| Silicon Dioxide, NF | 25.0 |
| p-toluene sulfonic acid, monohydrate, Sigma | 7.1 |
| Talc | 5.0 |
| Microcrystalline cellulose PH102, NF | 10.0 |
| Dry Granulation Composition | |
| Compound III (free base) | 13.3 |
| Propylene glycol, USP | 37.9 |
| Silicon Dioxide, NF | 25.9 |
| p-toluene sulfonic acid, monohydrate, Sigma | 7.3 |
| Talc | 5.2 |
| Microcrystalline cellulose PH102, NF | 10.4 |

EXAMPLE 10 (capsule)

| Component | % By Weight |
| --- | --- |
| Wet Granulation Composition | |
| Compound III (free base) | 16.8 |
| Propylene glycol, USP | 31.2 |
| Ethanol, dehydrated USP, 200 proof | 6.6 |
| Silicon Dioxide, NF | 30.0 |
| p-toluene sulfonic acid, monohydrate, Sigma | 9.3 |
| Talc | 1.0 |
| Microcrystalline cellulose PH102, NF | 5.0 |
| Dry Granulation Composition | |
| Compound III (free base) | 18.0 |
| Propylene glycol, USP | 33.4 |
| Silicon Dioxide, NF | 32.2 |
| p-toluene sulfonic acid, monohydrate, Sigma | 10.0 |
| Talc | 1.1 |
| Microcrystalline cellulose PH102, NF | 5.3 |

EXAMPLE 11 (capsule)

| Component | % By Weight |
| --- | --- |
| Compound III (free base) | 23.0 |
| Silicon dioxide, NF | 46.8 |
| Cremephore ® EL | 23.4 |
| Hydrochloric acid, reagent | 6.3 |

EXAMPLE 12 (capsule)

| Component | % By Weight |
| --- | --- |
| Wet Granulation Composition | |
| Compound III (free base) | 24.4 |
| Propylene glycol, USP | 8.5 |
| Ethanol, dehydrated USP, 200 proof | 17 |
| Citric acid, anhydrous | 3.7 |
| Polysorbate 80, NF | 8.5 |
| Vitamin E-PEG 1000 succinate | 2.1 |
| Hydrochloric acid, reagent grade | 1.8 |
| Cab-o-sil ® | 17 |
| Microcrystalline cellulose, PH102, NF | 17 |
| Dry Granulation Composition | |
| Compound III (free base) | 29.4 |
| Propylene glycol, USP | 10.2 |
| Citric acid, anhydrous | 4.5 |
| Polysorbate 80, NF | 10.2 |
| Vitamin E-PEG 1000 succinate | 2.5 |
| Hydrochloric acid, reagent grade | 2.2 |
| Cab-o-sil ® | 20.5 |
| Microcrystalline cellulose, PH102, NF | 20.5 |

EXAMPLE 13 (capsule)

| Component | % By Weight |
| --- | --- |
| Wet Granulation Composition | |
| Compound III (free base) | 21.6 |
| Propylene glycol, USP | 15.5 |
| Silicon dioxide, NF | 22.5 |
| Ethanol, dehydrated USP, 200 proof | 12.0 |
| Ascorbic acid, white powder | 2.3 |
| Polysorbate 80, NF | 4.4 |
| Cremophor ® EL | 4.4 |
| Hydrochloric acid, reagent grade | 2.2 |
| Microcrystalline cellulose, PH102, NF | 15.0 |
| Dry Granulation Composition | |
| Compound III (free base) | 24.5 |
| Propylene glycol, USP | 17.6 |
| Silicon dioxide, NF | 25.6 |
| Ascorbic acid, white powder | 2.6 |
| Polysorbate 80, NF | 5 |
| Cremophor ® EL | 5 |
| Hydrochloric acid, reagent grade | 2.5 |
| Microcrystalline cellulose, PH102, NF | 17 |

This composition can be prepared according to the following process. Propylene glycol (USP, 139 mL) and ethanol (dehydrated, USP, 200 proof, 139 mL) were mixed in a stainless steel or glass container. Hydrochloric acid (reagent grade, 20 mL) was added and mixed well. To this solution was added ascorbic acid (21 g) and the mixture was stirred until it was clear. Compound III (200 g) was slowly added to the solution and mixing was continued until the solution was clear. Cremophor® EL (41 g) and polysorbate 80, NF (41 g) were added with mixing.

Microcrystalline cellulose, NF (139 g) and silicon dioxide, NF (Syloid 244, pharmaceutical grade, 209 g) were charged into a Hobart mixer and mixed for 3–5 minutes. The above solution was added dropwise to the dry mixture in the Hobart mixer while mixing at slow speed. This mixture was massed until granular.

The wet granulation was screened through an 8 mesh screen. The screened granulation was spread on paper-lined trays and dried in a tray dryer or a fluidbed dryer (20°–35° C.) until the loss on drying was not more than 12%.

The concentration of compound III (mg/g of granulation) in the granulation was determined by HPLC analysis. Capsules (gelatin, No. 00, iron gray opaque) were filled with the appropriate amount of the dried granulation to provide the desired dose per capsule.

EXAMPLE 14 (Capsule)

| Component | % By Weight |
| --- | --- |
| Wet Granulation Composition | |
| Compound III (free base) | 21.6 |
| Propylene glycol, USP | 16.1 |
| Ethanol, dehydrated USP, 200 proof | 11.5 |
| Ascorbic acid, white powder | 2.3 |
| Polysorbate 80, NF | 4.4 |
| Cremophor ® EL | 4.4 |
| Hydrochloric acid, reagent grade | 2.1 |
| Cab-o-sil ® | 22.5 |
| Microcrystalline cellulose, PH102, NF | 15.1 |
| Dry Granulation Composition | |
| Compound III (free base) | 24.4 |
| Propylene glycol, USP | 18.2 |
| Ascorbic acid, white powder | 2.6 |
| Polysorbate 80, NF | 5.0 |
| Cremophor ® EL | 5.0 |
| Hydrochloric acid, reagent grade | 2.4 |
| Cab-o-sil ® | 25.4 |
| Microcrystalline cellulose, PH102, NF | 17.0 |

EXAMPLE 15 (capsule)

| Component | % By Weight |
| --- | --- |
| Compound III (free base) | 21.84 |
| Propylene glycol, USP | 10.96 |
| Ethanol, dehydrated USP, 200 proof | 22.99 |
| Polysorbate 80, NF | 5.31 |
| Cremophor ® EL | 4.4 |
| Hydrochloric acid, reagent grade | 1.18 |
| Cab-o-sil ® | 26.88 |

This composition was prepared according to the general procedure described above, with the exception that the granulation was not dried to remove the ethanol prior to filling the capsules.

EXAMPLE 16 (capsule)

| Component | % By Weight |
| --- | --- |
| Compound III (free base) | 22.02 |
| Propylene glycol, USP | 11.01 |
| Ethanol, dehydrated USP, 200 proof | 23.17 |
| Polysorbate 80, NF | 5.53 |
| Cremophor ® EL | 10.91 |
| Hydrochloric acid, reagent grade | 1.31 |
| Cab-o-sil ® | 19.54 |
| Maltodextrin | 6.51 |

This composition was prepared according to the general procedure described above, with the exception that the granulation was not dried to remove the ethanol prior to filling the capsules.

The remaining examples provide the preparation of compound III.

EXAMPLE 17

(2S,3S,5S)-5-(N-(N-((N-Methyl-N-((2-isopropyl-4-thiazolyl) methyl)amino)carbonyl)valinyl)amino)-2-(N-((5-thiazolyl) methoxycarbonyl)amino)-1,6-diphenyl-3-hydroxyhexane A. N-(((Benzyl)oxy)carbonyl)-L-phenylalaninal A solution of 24.5 ml of anhydrous dimethyl sulfoxide in 870 ml of anhydrous dichloromethane was cooled under $N_2$ atmosphere to −60° C. and treated over a period of 15 min with 131 ml of a 2M solution of oxalyl chloride in dichloromethane in order that the internal temperature remained below −50° C. After addition, the solution was stirred at −60° C. for 15 min and treated over a period of 20 min with a solution of 50 g (0.175 mol) of N-(((benzyl)oxy)-carbony)-L-phenylalaninol in 200 ml of dichloromethane. The resulting solution was stirred at −60° C. for 1 h, then treated over a period of 15 min with 97 ml of triethylamine in order that the internal temperature remained below −50° C. After addition the solution was stirred at −60° C. for 15 min, then, with the cooling bath in place, was treated rapidly (over a period of 1 min) with a solution of 163 g of citric acid in 550 ml of water. The resulting slurry was stirred vigorously for 10 min, allowed to warm, diluted to 1 liter with water, and separated. The organic layer was washed with 700 ml of water followed by a mixture of 550 ml of water and 150 ml of saturated aqueous $NaHCO_3$, dried over $MgSO_4$, and concentrated in vacuo at 20° C. to give the crude desired compound as a light yellow solid.

B. (2S,3R,4R,5S)-2,5-Bis-(N-(((benzyl)oxy)carbonyl) amino)-3,4-dihydroxy-1,6-dihenylhexane and (2S,3S,4S, 5S)-2,5-Bis-(N-(((benzyl)oxy)carbonyl)amino)-3,4-dihydroxy-1,6-diphenylhexane A suspension of 78.5 g of $VCl_3 \cdot (tetrahydrofuran)_3$ and 16 g of zinc dust in 400 ml of dry dichloromethane was stirred under $N_2$ atmosphere for 1 h at 25° C. A solution of 0.175 mol of N-(((benzyl)oxy)carbonyl)-L-phenylalaninal in 200 ml of dichloromethane was then added in one portion, and the resulting mixture was stirred at ambient temperature under $N_2$ atmosphere for 16 h. The resulting mixture was added to 500 ml of 1M aqueous HCl, diluted with 500 ml of hot chloroform, and shaked vigorously for 2 min. The layers were separated, and the organic layer was washed with 1M aqueous HCl and separated. Filtration of the organic phase provided the crude desired product as a solid residue. The residue was slurried in 1.25 liters of acetone, treated with 5 ml of concentrated $H_2SO_4$, and stirred for 16 h at ambient temperature. The resulting mixture was filtered, and the residue (residue A) was washed with 50 ml of acetone. The combined filtrate was concentrated to a volume of 250 ml, diluted with 1000 ml of dichloromethane, washed three times with water and once with saturated brine, dried over $MgSO_4$, and concentrated to give a viscous oil. The oil was taken up in 1000 ml of 1M HCl in methanol (prepared from 71 ml of acetyl chloride and 1000 ml of methanol) and stirred at ambient temperature for 2 h. The resulting precipitate was filtered, washed with methanol, and air-dried on the filter to provide 26.7 g of the desired compound as a white solid. The filtrate was concentrated and filtered to give a second crop (8.3 g) of 2S,3R,4R,5S)-2,5-bis-(N-(((benzyl)oxy)carbonyl)amino)-3,4-dihydroxy-1,6-diphenylhexane. $^1H$ NMR($d_6$-DMSO) δ 2.59 (dd, J=13, 5 Hz, 2H), 2.74 (dd, J=13, 9 Hz, 2H), 3.26 (br, 2H), 4.19(m, 2H), 4.54(m, 2H), 4.92(m, 4H), 6.82 (d, J=9 Hz, 2H), 7.0–7.35 (m, 20H). Mass spectrum: $(M+H)^+=569$.

Residue A (above, 2.65 g) was suspended in 75 ml of tetrahydrofuran (THF) and 75 ml of 1M aqueous HCl and heated at reflux for 24 h. After concentration of the resulting solution in vacuo, the residue was taken up in 10% methanol in chloroform, washed two times with water, dried over $Na_2SO_4$, and concentrated in vacuo to provide (2S,3S,4S, 5S)-2,5-bis-(N-(((benzyl)oxy)carbonyl)amino)-3,4-dihydroxy-1,6-diphenylhexane as a white solid. $^1H$ NMR($d_6$-DMSO) δ 2.64 (m, 2H), 3.04(m, 2H), 3.49(m, 2H), 3.78(m, 2H), 4.70 (d,J=7 Hz, 2H), 4.93 (AA', 4H), 7.1–7.4 (m, 20H). Mass spectrum: $(M+H)+=569$.

C. (2S,3R,4S,5S)-3-Acetoxy-2,5-bis-(N-(((benzyl)oxy)carbonyl) amino)-3-bromo-1,6-diphenylhexane A suspension of 25 g (44 mmol) of (2S,3R,4R,5S)-2,5-bis-(N-(( benzyl)oxy)carbonyl)amino)-3,4-dihydroxy-1,6-diphenylhexane in 500 ml of 2:1 dichloromethane/hexane was treated with 23 g of α-acetoxyisobutyryl bromide. The resulting mixture was stirred at ambient temperature until the reaction clarified, washed with two 200 ml portions of saturated aqueous $NaHCO_3$, dried over $MgSO_4$, and concentrated in vacuo to give 30.8 g of the crude desired compound. A portion was purified by silica gel chromatography using 9:1 dichloromethane:ethyl acetate to provide the pure desired compound as a white solid. $^1H$ NMR ($CDCl_3$) δ 2.21 (s, 3H), 2.62 (dd, J=13, 11 Hz, 1H), 2.75(d,J=7 Hz, 2H), 2.95 (br d, J=15 Hz, 1H), 4.03 (br t, J=10 Hz, 1 h), 4.40 (br d, J=10 Hz, 1H), 4.6–5.0 (m, 6H), 5.12 (br d, J=13 Hz, 1H), 5.33 (br d, J=11 Hz, 1H), 7.0–7.4 (m, 10H). Mass spectrum: $(M+NH_4)^+=690,692$.

D. (2S,3R,4R,5S)-2,5-Bis-(N-(((benzyl)oxy)Carbonyl)amino)-3,4-epoxy-1,6-diphenylhexane A solution of 35.56 g (52.8 mmol) of (2S,3R,4S,5S)-3-acetoxy-2,5-bis-(N-(((benzyl)oxy)carbonyl)amino)-3- bromo-1,6-diphenylhexane in 375 ml of dioxane was treated with 255 ml of 1N aqueous sodium hydroxide and stirred at ambient temperature for 16 h, during which the desired compound precipitated. The resulting mixture was filtered, and the residue was washed with water and dried to provide 22.23 g (76%) of the desired compound as a white solid. $^1$H NMR (CDCl$_3$) δ 2.7–2.9 (m, 6H), 3.9–4.0 (m, 2H), 4.6–4.7 (m, 2H), 5.03 (m, 4H), 7.1–7.4 (m, 10H).

E. (2S,3S,5S)-2.5-Bis-(N-(((benzyl)oxy)carbonyl)amino)-1,6-diphenyl-3-hydroxyhexane A mixture of 39.2 g (71.2 mmol) of 2S,3R,4R,5S)-2,5-bis-(N-(((benzyl)oxy)carbonyl)amino)-3,4-epoxy-1,6-diphenylhexane in 600 ml of THF was treated under N$_2$ atmosphere with 13 g (0.36 mol) of sodium borohydride. The resulting mixture was treated dropwise with 27.7 ml (0.36 mol) of trifluoroacetic acid. After being stirred for 3.5 h at ambient temperature, the resulting mixture was quenched with 1N aqueous HCl, diluted with water, and stirred for 16 h. The resulting mixture was filtered. washed with water, and dried to provide 22.85 g (58%) of the desired compound as a white solid.

F. (2S,3S,5S)-2,5-Diamino-1,6-diphenyl-3-hydroxyhexane

A suspension of 32 g of the crude resultant compound of Example 17E and 55.5 g (176 mmol) of barium hydroxide octahydrate in 400 ml of 1,4-dioxane and 400 ml of water was heated at reflux for 4 h. The resulting mixture was filtered, and the residue was rinsed with dioxane. The combined filtrates were concentrated to a volume of approximately 200 ml and extracted with four 400 ml portions of chloroform. The combined organic layers were dried over Na$_2$SO$_4$, filtered, and concentrated in vacuo. The residue was purified by silica gel chromatography using first 2% isopropylamine in chloroform and then 2% isopropylamine/2% methanol in chloroform to provide 10.1 g (81%) of the pure desired compound as a white solid. $^1$H NMR (CDCl$_3$) δ 1.54 (dt, J=14, 10 Hz, 1H), 1.67 (dt, J=14, 3 Hz, 1H), 2.50 (dd, J=13, 8 Hz, 1H), 2.58 (dd, J=13, 8Hz, 1H), 2.8 (m, 2H), 2.91 (dd, J=13, 5 Hz, 1H), 3.10(m, 1H), 3.72 (ddd, J=11, 3, 2 Hz, 1H), 7.1–7.4 (m, 10H). Mass spectrum: (M+H)$^+$=285.

G. (4S,6S,1'S)-6-(1-Amino-2-phenylethyl)-4-benzyl-2-phenyl-3-aza-2-bora-1-oxacyclohexane A solution of 11.28 g (40 mmol) of (2S,3S,5S)-2,5-diamino-1,6-diphenyl3-hydroxyhexane and 4.88 g (40 mmol) of phenylboric acid in 1 liter of toluene was heated at reflux and the water azeotropically removed with the aid of a Dean Stark trap until the distillate was clear. The solvent was then removed in vacuo to provide the crude desired compound which was used immediately without further purification.

H. Thioformamide

To a cooled (0° C.) 2 L three neck round bottom flask equipped with an overhead stirrer charged with a solution of formamide (30.5 mL, 0.76 mol) in 1 L of diethyl ether was added 89 g (0.19 mol) of phosphorous pentasulfide in small portions. The reaction mixture was allowed to warm to ambient temperature, stirred for 2 h, filtered, and concentrated in vacuo to afford thioformamide as a yellow offensive smelling oil which was used without purification.

I. Ethyl 2-Chloro-2-formylacetate

To a three neck 2 L round bottom flask charged with potassium t-butoxide (0.5 mol, 500 mL of a 1M solution in THF) and 500 mL of dry THF cooled to 0° C. was added dropwise from an addition funnel a solution of ethyl chloroacetate (0.5 mol, 53.5 mL) and ethyl formate (0.5 mol, 40.4 mL), in 200 mL of THF over 3 hours. After completion of addition, the reaction mixture was stirred for 1 hour and allowed to stand overnight. The resulting solid was diluted with diethyl ether and cooled in an ice bath. Then, the pH was lowered to approximately 3 using 6N HCl. The organic phase was separated, and the aqueous layer was washed 3 times with diethyl ether. The combined ethereal portions were dried over NaSO$_4$, and concentrated in vacuo. The crude desired compound was stored at –30° C. and used without further purification.

J. Ethyl Thiazol-5-carboxylate

To a round bottom flask was added 250 mL of dry acetone, 7.5 g (0.123 mol) of thioformamide, and 18.54 g (0.123 mol) of ethyl 2-chloro-2 formylacetate. The reaction was heated at reflux for 2 hours. The solvent was removed in vacuo, and the residue was purified by chromatography (SiO$_2$, 6 cm o.d. column, 100% CHCl$_3$, R$_f$=0.25) to provide 11.6 g (60%) of the desired compound as a light yellow oil. NMR (CDCl$_3$) δ 1.39 (t, J=7 Hz, 3H), 4.38 (q, J=7 Hz, 2H), 8.50(s, 1H), 8.95(s, 1H).

K. 5-(Hydroxymethyl)thiazole

To a precooled (ice bath) three neck 500 mL flask containing lithium aluminum hydride (76 mmol) in 250 mL of THF was added ethyl thiazole-5 carboxylate (11.82 g, 75.68 mmol) in 100 mL of THF dropwise over 1.5 hours to avoid excess foaming. The reaction was stirred for an additional hour, and treated cautiously with 2.9 mL of water, 2.9 mL of 15% NaOH, and 8.7 mL of water. The solid salts were filtered, and the filtrate set aside. The crude salts were heated at reflux in 100 mL of ethyl acetate for 30 min. The resulting mixture was filtered, and the two filtrates were combined, dried over Na$_2$SO$_4$, and concentrated in vacuo. The product was purified by silica gel chromatography eluting sequentially with 0%–2%–4% methanol in chloroform, to provide the desired compound, Rf=0.3 (4% methanol in chloroform), which solidified upon standing in 75% yield. NMR (CDCl$_3$) δ 4.92(s, 2H), 7.78(s, 1H), 8.77 (s, 1H). Mass spectrum: (M+H)$^+$=116.

L. ((5-Thiazolyl)methyl)-(4-nitrophenyl)carbonate

A solution of 3.11 g (27 mmol) of 5-(hydroxymethyl)thiazole and excess N-methyl morpholine in 100 ml of methylene chloride was cooled to 0° C. and treated with 8.2 g (41 mmol) of 4-nitrophenyl chloroformate. After being stirred for 1h, the reaction mixture was diluted with CHCl$_3$, washed successively with 1 N HCl, saturated aqueous NaHCO$_3$, and saturated brine, dried over NaSO$_4$, and concentrated in vacuo. The residue was purified by silica gel chromatography (SiO2, 1–2% MeOH/CHCl$_3$, Rf=0.5 in 4% MeOH/CHCl$_3$) to yield 5.9 g (78%) of the desired compound as a yellow solid. NMR (CDCl$_3$) δ 5.53 (s, 2H), 7.39 (dt, J=9, 3 Hz, 2H), 8.01 (s, 1H), 8.29 (dt, J=9, 3 Hz, 2H), 8.90 (s, 1H). Mass spectrum: (M+H)$^+$=281.

M. (2S,3S,5S)-5-Amino-2-(N-((5-thiazolyl)methoxycarbonyl) amino)-1,6-diphenyl-3-hydroxyhexane and (2S,3S,5S)-2-Amino-5-(N-( (5-thiazolyl)-methoxycarbonyl)amino-1,6-diphenyl-3-hydroxyhexane A solution of 500 mg (1.76 mmol) of (2S,3S,5S)-2,5-diamino-1,6-diphenyl-3-hydroxyhexane and 480 mg (1.71 mmol) of ((5-thiazolyl)methyl)-(4-nitrophenyl)carbonate in 20 ml of THF was stirred at ambient temperature for 4 h. After removal of the solvent in vacuo, the residue was purified by silica gel chromatography using first 2% then 5% methanol in chloroform to provide a mixture of the two desired compounds. Silica gel chromatography of the mixture using a gradient of 0–1–2% methanol in 93:2 isopropylamine: chloroform provided 110 mg (16%) of (2S,3S, 5S)-5-amino-2-(N-((5-thiazolyl)-methoxycarbonyl)amino )-1,6-diphenyl-3- hydroxyhexane (R$_f$0.48, 96:2:2 chloroform:methanol:isopropylamine) and 185 mg (28%) of (2S, 3S,5S)-2-amino-5-(N-((5-thiazolyl)methoxycarbonyl) amino)-1,6-diphenyl-3-hydroxyhexane ($R_f$ 0.44, 96:2:2 chloroform:methanol:isopropylamine).

(2S,3S,5S)-5-Amino-2-(N-((5-thiazolyl)methoxycarbonyl)amino)-1,6-diphenyl-3-hydroxyhexane: NMR ($CDCl_3$) δ 1.3–1.6 (m, 2H), 2.40(dd, J=14, 8 Hz, 1H), 2.78 (dd, J=5 Hz, 1H), 2.88 (d, J=7 Hz, 2H), 3.01(m, 1H), 3.72 (br q, 1H), 3.81 (br d, J=10 Hz, 1H), 5.28 (s, 2H), 5.34(br d, J=9 Hz, 1H), 7.07 (br d, J=7 Hz, 2H), 7.15–7.35 (m, 8H), 7.87 (s, 1H), 8.80 (s, 1H). Mass spectrum: $(M+H)^+$=426.

(2S,3S,5S )-2-Amino-5-(N-((5-thiazolyl)methoxycarbonyl)amino)-1,6-diphenyl3-hydroxyhexane: NMR ($CDCl_3$) δ 1.55 (dt, J=14, 8 Hz, 1H), 1.74 (m, 1H), 2.44 (dd, J=15, 1 Hz, 1H), 2.75–3.0 (m, 4H), 3.44 (m, 1H), 4.00 (br t, 1H), 5.28 (m, 3H), 7.1–7.4 (m, 10H), 7.86 (s, 1H), 8.80 (s, 1H). Mass spectrum: $(M+H)^+$=426.

N. (2S,3S,5S)-5-Amino-2-(N-((5-thiazolyl)methoxycarbonyl) amino)-1,6-diphenyl-3-hydroxyhexane A solution of 40 mmol of crude (4S,6S,1'S)-6-(1-amino-2-phenylethyl)-4-benzyl-2-phenyl-3-aza-2-bora-1-oxacyclohexane in 700 ml of anhydrous THF was cooled to −40° C. and treated dropwise over a period of 1 h with a solution of 7.83 g (27.9 mmol) of ((5-thiazolyl)methyl)-(4-nitrophenyl)carbonate in 300 ml of dry THF. The resulting solution was allowed to warm to 0° C. for 3 h, then to ambient temperature for 16 h. The solvent was removed in vacuo, and the residue was taken up in 700 ml of ethyl acetate, washed with three 150 ml portions of 1N aqueous NaOH and one 150 ml portion of brine. The organic phase was dried over $Na_2SO_4$ and concentrated in vacuo. Purification of the residue by silica gel chromatography using methanol/chloroform mixtures provided the desired compound mixed with its regioisomer. A second chromatography using 1–3% isopropylamine in chloroform provided 5.21 g of the desired compound which solidified upon standing.

O. 2-Methylpropane-thioamide

A suspension of 100 g (1.15 mol) of isobutyramide in 4L of diethyl ether was stirred vigorously and treated in portions with 51 g (0.115 mol) of $P_4S_{10}$. The resulting mixture was stirred at ambient temperature for 2 h, filtered, and concentrated in vacuo to provide 94.2 g (80%) of the crude desired compound. 1H NMR (DMSO-$d_6$) δ 1.08 (d, J=7 Hz, 6H), 2.78 (heptet, J=7 Hz, 1H), 9.06 (br, 1H), 9.30 (br, 1H). Mass spectrum: $(M+H)^+$=104.

P. 4-(Chloromethyl)-2-isopropylthiazole hydrochloride

A mixture of 94.0 g (0.91 mol) of 2-methylpropane-thioamide, 115.7 g (0.91 mol) of 1,3-dichloroacetone, and 109.7 g (0.91 mol) of $MgSO_4$ in 1.6 liters of acetone was heated at reflux for 3.5 h. The resulting mixture was allowed to cool, filtered, and the solvent was removed in vacuo to provide the crude desired compound as a yellow oil. $^1$H NMR (DMSO-$d_6$) δ 1.32 (d, J=7 Hz, 6H), 3.27 (heptet, J=7 Hz, 1H), 4.78 (s, 2H), 7.61 (s, 1H). Mass spectrum: $(M+H)^+$=176.

Q. 2-Isopropyl-4-(((N-methyl)amino)methyl)thiazole

A solution of 40 g of 4-(chloromethyl)-2-isopropylthiazole hydrochloride in 100 ml of water was added dropwise with stirring to 400 ml of 40% aqueous methylamine. The resulting solution was stirred for 1 h, then concentrated in vacuo. The residue was taken up in chloroform, dried over $Na_2SO_4$, and concentrated in vacuo. Purification of the residue by silica gel chromatography using 10% methanol in chloroform provided 21.35 g (55%) of the desired compound. $^1$H NMR (DMSO-$d_6$) δ 1.34(d, J=7 Hz, 6H), 2.56 (s, 3H), 3.30 (heptet, J=7 Hz, 1H), 4.16 (s, 2H), 7.63 (s, 1H). Mass spectrum: (M+H)+=171.

R. N-(((4-Nitrophenyl)oxy)carbonyl)-L-valine Methyl Ester

A solution of 66.1 g (0.328 mol) of 4-nitrophenyl chloroformate in 1.2 liters of $CH_2Cl_2$ was cooled to 0° C. and treated with L-valine methyl ester hydrochloride. The resulting mixture was treated slowly, with stirring, with 68.9 ml (0.626 mol) of 4-methylmorpholine. The resulting solution was allowed to slowly warm to ambient temperature and was stirred overnight. After washing with 3 portions of 10% aqueous $NaHCO_3$, the solution was dried over $Na_2SO_4$ and concentrated in vacuo. The residue was purified by silica gel chromatography by eluting with chloroform to provide the desired compound. $^1$H NMR (DMSO-$d_6$) δ 0.94 (d, J=7 Hz, 3H), 0.95 (d, J=7 Hz, 3H), 2.12 (octet, J=7 Hz, 1H), 3.69 (s, 3H), 4.01 (dd, J=8, 6 Hz, 1H), 7.41 (dt, J=9, 3 Hz, 2H), 8.27 (dt, J=9, 3 Hz, 2H), 8.53 (d, J=8 Hz, 1H). Mass spectrum: $(M+NH_4)^+$=314.

S. N-((N-Methyl-N-((2-isopropyl-4-thiazolyl)methyl)amino)carbonyl)-L-valine Methyl Ester A solution of 15.7 g (92 mmol) of 2-isopropyl-4-(((N-methyl)amino)-methyl)thiazole in 200 ml of THF was combined with a solution of 20.5 g (69 mmol) of N-(((4-nitrophenyl)oxy)carbonyl)-L-valine methyl ester. The resulting solution was treated with 1.6 g of 4-dimethylaminopyridine and 12.9 ml (92 mmol) of triethylamine, heated at reflux for 2 h, allowed to cool, and concentrated in vacuo. The residue was taken up in $CH_2Cl_2$, washed extensively with 5% aqueous $K_2CO_3$, dried over $Na_2SO_4$, and concentrated in vacuo. The resulting product mixture was purified by silica gel chromatography using chloroform as an eluent to provide 16.3 g (54%) of the desired compound. $^1$H NMR (DMSO-$d_6$) δ 0.88 (d, J=7 Hz, 3H), 0.92 (d, J=7 Hz, 3H), 1.32 (d, J=7 Hz, 3H), 2.05 (octet, J=7 Hz, 1H), 2.86 (s, 3H), 3.25 (heptet, J=7 Hz, 1H), 3.61 (s, 3H), 3.96 (dd, J=8, 7 Hz, 1H), 4.44 (AA', 2H), 6.58 (d, J=8 Hz, 1H), 7.24 (s, 1H). Mass spectrum: $(M+H)^+$=328.

T. N-((N-Methyl-N-((2-isopropyl-4-thiazolyl)methyl)amino)carbonyl)-L-valine

A solution of 1.42 g (4.3 mmol) of the resultant compound of Example 17S in 17 ml of dioxane was treated with 17.3 ml of 0.50M aqueous LiOH. The resulting solution was stirred at ambient temperature for 30 min, treated with 8.7 ml of 1M HCl, and concentrated in vacuo. The residue was taken up in dichloromethane, washed with water, dried over $Na_2SO_4$, and concentrated in vacuo to provide 1.1 g (81%) of the desired compound. Mass spectrum: $(M+H)^+$=314.

U. (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane A solution of 70 mg (0.223 mmol) of N-((N-methyl-N-((2-isopropyl-4-thiazolyl)methyl)amino)carbonyl)-L-valine, 79 mg (0.186 mmol) of (2S,3S,5S)-5-amino-2-(N-((5-thiazolyl)methoxycarbonyl)amino)-1,6-diphenyl-3-hyddroxyhexane, 30 mg (0.223 mmol) of 1-hydroxybenzotriazole hydrate, and 51 mg (0.266 mmol) of N-ethyl-N'-dimethylaminopropyl carbodiimide in 2 ml of THF was stirred at ambient temperature for 16 h. The resulting solution was concentrated in vacuo, and the residue was purified by silica gel chromatography using 97:3 $CH_2Cl_2$: $CH_3OH$ to provide 100 mg (74%) of the desired compound ($R_f$ 0.4, 95:5 $CH_2Cl_2$: $CH_3OH$) as a solid, mp 61°–63° C. Mass spectrum: $(M+H)^+$=721. Anal. Calcd for $C_{37}H_{49}N_6O_5S_2 \cdot 0.5H_2O$: C, 60.88; H, 6.77; N, 11.51. Found: C, 60.68; H, 6.53; N, 11.36.

EXAMPLE 18

(2S,3S,5S)-2-Amino-3-hydroxy-5-(t-butyloxycarbonylamino)-1,6-diphenylhexane

EXAMPLE 18 A (2S,3S,5S)-2-(N,N-dibenzylamino)-3-hydroxy-5-(t-butyloxycarbonylamino)-1,6-diphenylhexane To a stirred solution of (2S,3S,5S)-2-(N,N-dibenzylamino)-3-hydroxy-5-amino-1,6-diphenylhexane (10.0 g, 21,6 mmol)in tetrahydrofuran (200 mL) was added potasium carbonate (6.0 g, 43.2 mmol)in $H_2O$ (200 mL). To this solution was added di-t-butyldicarbonate (5.64 g, 25.9 mmol) in tetrahydrofuran (10 mL). The solution which resulted was stirred at room temperature for 3 hours. N,N-dimethylethylenediamine (1 mL, 8.6 mmol) was added and the reaction mixture was stirred at room temperature for an additional hour. Ethyl acetate (400 mL) was added and the organic layer was separated and washed with 5% $KH_2PO_4$ (2×200 mL), water (1×200 mL), saturated $NaHCO_3$ (2×200 mL) and water (1×200 mL). The organic solution was then dried over sodium sulfate and concentrated under reduced pressure to provide the desired product as a light yellow oil. 300 MHz $_1H$ NMR (CDCl$_3$)$\delta$ 1.40 (s, 9H), 1.58 (s, 2H), 2.45–2.85 (m, 4H), 3.05 (m, 1H), 3.38 (d, 2H), 3.6 (m, 1H), 3.79 (m, 1H), 3.87 (d, 2H), 4.35 (s, 4H), 4.85 (s, broad, 1H), 7.0–7.38 (m, 20H).

EXAMPLE 18B (2S,3S,5S)-2-amino-3-hydroxy-5-(t-butyloxycarbonylamino)-1,6-diphenylhexane To a stirred solution of (2S,3S,5S)-2-(N,N-dibenzylamino)-3-hydroxy-5-(t-butyloxycarbonylamino)-1,6-diphenylhexane (12 g, 21.3 mmol)in methanol (350 mL) was charged ammonium formate (8.05 g, 128 mmol, 6.0 eq) and 10% palladium on carbon (2.4 g). The solution was stirred under nitrogen at 60° C. for three hours and then at 75° C. for 12 hours. An additional amount of ammonium formate (6 g) and 10% palladium on carbon (1.5 g) was added as well as 1 mL of glacial acetic acid. The reaction was driven to completion within 2 hours at a reflux temperature. The reaction mixture was then cooled to room temperature and then filtered through a bed of celite. The filter cake was washed with methanol (75 mL) and the combined filtrates were concentrated under reduced pressure. The residue was taken up in 1N NaOH (300 mL) and extracted into methylene chloride (2×200 mL). The combined organic layers were washed with brine (250 mL) and dried over sodium sulfate. Concentration of the solution under reduced pressure provided the desired product as a light colored oil which slowly crystallized upon standing (5 g). Further purification of the product could be accomplished by flash chromatography (silica gel, 5% methanol in methylene chloride). 300MHz $^1H$ NMR (CDCl$_3$) $\delta$ 1.42 (s, 9H), 1.58 (m, 1H), 1.70 (m, 1H), 2.20 (s, broad, 2H), 2.52 (m, 1H), 2.76–2.95 (m, 4H), 3.50 (m, 1H), 3.95 (m, 1H), 4.80 (d, broad, 1H), 7.15–7.30 (m, 10H).

EXAMPLE 19

Alternative Preparation of (2 S,3S,5 S)-2-Amino-3-hydroxy-5-(t-butyloxycarbonylamino)-1,6-diphenyl-hexane

EXAMPLE 19A (5S )-2-( t-Butyloxycarbonylamino)-5-(N,N-dibenzylamino )-1,6-diphenyl-4-oxo-2-hexene To 9.21 gm (20 mmol) of (S)-2-amino-5-(N,N-dibenzylamino)-1,6-diphenyl-4-oxo-2-hexene and 0.37 gm (3 mmol) 4-N,N-dimethylaminopyridine in 100 ml of methyl tert-butylether was added via syringe pump a solution containing 4.80 gm (22 mmol) di-tert-butyl dicarbonate in the same solvent (25 ml) over a period of 6 h. An additional amount (3 ml) of methyl tert-butylether was then added to complete the addition. After stirring at room temperature for 18 h the reaction mixture was cooled with the aid of an ice water bath. The resultant solid was collected by suction filtration and washed with cold (0° C.) methyl tert-butylether and hexane and dried under vacuum to give 9.9 gm of crude material as a white solid. The material thus isolated was disolved in a minimal amount of dichloromethane and purified by flash chromatography on silica gel. Elution of the column with a mixture of hexane-ethyl acetate-dichloromethane (8:1:1) gave, after concentration of the appropriate fractions, 8.1 gm (72%) of the desired compound. Mp. 191°–193° C. [$\alpha$]$_D$ –183.7° (c=1.05, CHCl$_3$). $^1H$ NMR (CDCl$_3$, $\delta$): 11.68 (bs, 1H), 7.05–7.47 (m, 20H), 5.28 (s, 1H), 4.27 (d, J=1 6 Hz, 1H), 4.02(d, J=1 6 Hz, 1H), 3.58(m, 4H), 3.40(m, 1H), 3.11 (m, 1H), 2.90 (m, 1H), 1.48 (s, 9H).

EXAMPLE 19B

Alternate preparation of (5 S)-2-( t-Butyloxycarbonylamino)-5-(N,N-dibenzylamino)-1,6-diphenyl-4-oxo-2-hexene A suspension of (S)-2-amino-5-(N,N-dibenzylamino)-6, 1-diphenyl-4-oxo-2-hexene (100.0 g, 0.217 mol) in 15% ethyl acetate/hexanes (2 liters) under $N_2$ was warmed to about 40° C. The resulting solution was cooled to room temperature before adding 4.0 g (33 mmol) of N,N-dimethyl-4-aminopyridine and 49.7 g (0.228 mol) of di-tert-butyl dicarbonate. The reaction mixture was allowed to stir overnight at room temperature. (After approximately one hour, a white precipitate began to form.) The suspension was filtered and the precipitate was washed with hexanes to afford the desired product as colorless crystals. TLC: 25% ethyl acetate/hexanes R$_f$ 0.38.

EXAMPLE 19C (2S,3S,5S)-2-(N,N-Dibenzylamino)-5-(t-butyloxycarbonylamino)-3-hydroxy-1,6-diphenylhexane A solution of the product of Example 19A (5 g, 8.9 mmol) in dichloromethane (100 ml) and 1,4-dioxolane (100 ml) was cooled to between –10° and –15° C. and treated dropwise with 1M BH$_3$THF (26.7 ml, 26.7 mmol). The solution was stirred at this temperature for 3 hr. The clear solution was quenched with excess methanol (20 ml) and stirred at room temperature for 30 min. The solvent was removed in vacuo.

The resulting white foam was dissolved in THF (75 ml) and cooled to –40° C. A solution of LAH (9 ml, 1M in THF, 9 mmol) was added dropwise. After 10 min. the solution was quenched with water followed by dilute aqueous HCl. The organics were removed and the aqueous layer extracted with ethyl acetate (3×20 ml). The combined organics were washed (saturated aqueous bicarbonate followed by brine), dried (Na$_2$SO$_4$), filtered and evaporated to afford 4.9 g (99%) of the desired product as a white foam.

Alternatively, the white foam resulting from the BH$_3$THF reaction step was dissolved in MeOH (45 ml), cooled to +3° C. and treated portionwise with KBH$_4$ (1.44 g, 26.7 mmol). After addition of the last portion of KBH$_4$ the reaction was stirred for an additional 4 hours at +4 to +5° C. The solution was concentrated by ½ the volume in vacuo, diluted with 1/1 hexane-EtOAc (70 ml) and quenched (with cooling, maintain temp. <30° C.) by adding a 10% solution of $KHSO_4$ to pH=about 5. NaOH (15% aqueous) was added to pH=12–13. The insoluble salts were removed by filtration, and the filter cake washed 3 times with 7 ml 1/1 hexane/EtOAc. The filtrate and washes were transferred to a separatory funnel, diluted with 15 ml hexane and 15 ml $H_2O$. The organics were removed and the aqueous layer was extracted once with 20 ml (1/1) hexane-EtOAc. The combined organics were washed (saturated brine), dried ($Na_2SO_4$), filtered, and evaporated to afford 5.2 g of the desired product which was used without further purification in subsequent reactions. $R_f$ 0.5 (25% EtOAc/hexane) 1H NMR ($CDCl_3$) δ 7.37–7.10(m 20H); 6.78 (br. s, 1H); 4.62(d, 1H); 4.50 (s, 1H); 4.18 (dd, 1H); 3.9 (d, 2H); 3.65 (dd, 2H); 3.40 (d, 2H); 3.00 (m, 2H); 2.77 (m, 1H); 1.39(s, 9H). MS (EI) m/e565 (M+H).

EXAMPLE 19D (2S,3S,5S)-2-Amino-3-hydroxy-5-(t-butyloxycarbonylamino)-1,6-diphenylhexane A solution of the product from Example 19C (150 gm, 250 mmol) dissolved in absolute EtOH (2 liters) was treated with 10% Pd/C (18 gm, prewetted), followed by addition of ammonium formate (78.6 gms, 1.25 moles) dissolved in $H_2O$ (200 ml). The resulting mixture was stirred at reflux for 2.5 hours. The mixture was cooled to room temperature and filtered through a pad of infusorial earth (20 g). The filter cake was washed 3 times with EtOH (70 ml each). The filtrate was concentrated/n vacuo. The residue was dissolved into EtOAc (1L) and washed (1N NaOH, followed by $H_2O$, followed by brine), dried ($Na_2SO_4$), filtered and concentrated/n vacuo. to a constant weight of 95 gms. (99.2% of theory). The light yellow solid (91.5 gm of the 95 gm) was slurried in hot heptane (600 ml) (steam bath) and treated with isopropanol (45 ml), and swirled to effect solution. The solution was allowed to slowly cool to room temperature over 3 hours, kept at room temperature for 2 more hours and filtered. The filter cake was washed 10 times with 9/1 hexane-isopropanol (30 ml each) to give the desired product as an off-white finely crystalline solid which was dried to constant weight of 57.5 gm.

The crude product (20 gm) was recrystallized from hot 140 ml heptane/17 ml isopropanol. After letting the solution cool slowly to room temperature, the mixture was let stand at room temperature for 2 hours and then filtered. The filter cake was rinsed (5×15 ml (8/1) heptane/isopropanol) and dried to a constant weight of 18.5 gm.

EXAMPLE 20

Alternative Preparation of (2S,3S,5S)-5-(N-(N-((N-Methyl-N-((-2-isopropyl-4-thiazolyl)methyl)amino)carbonyl)valinyl)amino)-2-(N-((5-thiazolyl) methoxycarbonyl)amino)-1,6-diphenyl-3-hydroxyhexane

EXAMPLE 20A (2S,3S,5S)-5-(t-Butyoxycarbonylamino)-2-(N-((5-thiazolyl)methoxycarbonyl)amino)-1,6-diphenyl-3-hydrdoxyhexane The product of Example 19D (6.0 g, 15.6 mmoles) was dissolved in 60 mL of DMF under nitrogen atmosphere. To this stirred solution at room temperature was added 5-(p-nitrophenyloxycarbonyloxymethyl)thiazole (4.67 g, 15.6 mmole) and the resulting solution was stirred for 4 h. The solvent was removed under reduced pressure by rotary evaporation and the residue dissolved in 150 mL EtOAc. This solution was washed with 5×75 mL 1N NaOH solution, 100 mL brine, dried over $NA_2SO_4$. The solvent was removed to afford 8.02 g of a slightly yellowish oil. This material was crystallized from 30 mL EtOAc and 40 mL hexane to afford 6.53 g (80%) of the desired product as a white solid. mp 118°–120° C. H $^1$NMR ($CDCl_3$) δ 8.79 (s, 1H), 7.83 (s, 1H), 7.30–7.15 (m, 8H), 7.08 (m, 2H), 5.23 (s, 2H), 5.14 (d, 1H, J=9 Hz), 4.52 (m, 1H), 3.92–3.72 (m, 3H), 3.65 (m, 1H), 2.85 (d-apparent, 2H, J=7.5 Hz), 2.72 (d-apparent, 2H, J=7 Hz), 1.61 (m, 2H), 1.38 (s, 9H). CIMS m/z (526) (M+H)$^+$, 543 (M+18)$^+$.

EXAMPLE 20B (2S,3S,5S)-5-Amino-2-(N-((5-thiazolyl)methoxycarbonyl)amino)-1,6-diphenyl-3-hydroxyhexane The product of Example 20A (6.43 g, 12.23 mmoles) was dissolved in 25 mL dioxane at room temperature under nitrogen atmosphere. To this stirred solution was added 20.25 mL of 4N HCl in dioxane, and after approximately 10 min a thick precipitate formed. An additional 10 mL of dioxane was added to loosen up the slurry. This mixture was stirred for 1 h and then filtered. The filter cake of the product bis-HCl salt was washed with 20 mL dioxane, air dried, and then dissolved in 175 mL water. To this solution was added 175 mL ethyl acetate and the two phase mixture rapidly stirred. The pH of this mixture was adjusted to pH=10 by the dropwise addition of 3N NaOH to the rapidly stirred mixture. The organic layer was isolated, washed with brine (150 mL), and dried over $NA_2SO_4$. The solvent was removed to afford 5.18 g (99%) of the desired product as a clear oil. H$^1$NMR ($CDCl_3$) δ 8.81 (s, 1H), 7.87 (s, 1H), 7.35–7.05 (m, 10H), 5.33(d, 1H, J=9.3 Hz), 5.28 (m, 2H), 3.81 (m, 1H), 3.72 (m, 1H), 3.01 (m, 1H), 2.88 (m, 2H), 2.78 (dd, 1H, J=13.5, 5.1 Hz), 2.39(dd, 1H, J=9.0, 4.5 Hz), 1.57–1.30 (m, 2H). CIMS m/z 426(M+H)$^+$.

EXAMPLE 20C (2S,3S,5S )-5-(N-(N-((N-Methyl-N-((2-isopropyl-4-thiazolyl) methyl)amino)carbonyl)valinyl)amino)-2-(N-((5-thiazolyl) methoxycarbonyl)amino)-1,6-diphenyl-3-hydroxyhexane N-((N-Methyl-N-((2-isopropyl-4-thiazolyl)methyl)amino)carbonyl)-L-valine (4.13 g, 13.18 mmole) and hydroxybenztriazole (2.23 g, 16.48 mmoles) were dissolved in 70 mL THF and then dicyclohexyl-carbodiimide(2.71 g, 13.18mmoles) was added in one portion to the stirred solution under nitrogen atmosphere. This mixture was stirred for 4 h at room temperature and then filtered to remove dicyclohexylurea precipitate. (2S,3S,5S)-5-Amino-2-(N-((5-thiazolyl)-methoxycarbonyl)amino)-1,6-diphenyl-3-hydroxyhexane (5.1 g, 11.99 mmoles) was dissolved in 100 mL THF under nitrogen atmosphere. To this stirred solution was added the filtrate of HOBT-active ester and the resulting solution was stirred at room temperature for 4 h, and the solvent removed via rotary evaporation. The residue was dissolved in 150 mL ethyl acetate and washed with 2×100 mL 1N NaOH, 100 mL brine, 100 mL of 1% w/w aqueous $KHSO_4$ and the solvent was removed by rotary evaporation to afford a residue. The residue was dissolved in 175 mL 1N HCL, and the solution filtered to remove the small quantity of dicyclohexylurea. The filtrate solution was added to 175 mL ethyl acetate and the two phase mixture rapidly mixed. The pH of this rapidly stirred mixture was adjusted to pH=7 by dropwise addition of cold 3N NaOH. The organic layer was isolated, washed with 100 mL brine, dried over $Na_2SO_4$, filtered, and the solvent was removed to afford 8.6 g of a colorless foam. This material was crystallized from 42 mL EtOAc and 21 mL hexane to give 7.85 g of the desired product as a white solid. mp=122°–123° C. CIMS m/z 721(M+H) $^+$.

EXAMPLE 21

Alternative Preparation of (2S,3S,5S)-5-Amino-2-(N-((5-thiazolyl)methoxycarbonyl)amino)-1,6-diphenyl-3-hydrohexane Alternative A The product of Example 17F (9.5 g, 33.4 mmol) and phenylboronic acid (4.1 g, 33.6 mmol) were combined in toluene (150 mL) and refluxed for 2.5 hours with azeotropic water removal (Dean-Stark trap). Toluene (100 mL) was distilled out at atmospheric pressure, then the remaining toluene was removed under vacuum, to provide a yellow syrup which was dissolved in DMF (50 mL) and cooled to –60° C. A solution of 5-(p-nitrophenyloxycarbonyloxy-methyl)thiazole (9.5 g, 33.5 mmol) in DMF (50 mL) was added over 45 minutes. The resulting mixture was stirred for 8 hours at –55°±5° C., then 14 hours at –25° C., then was allowed to warm to room temperature. The reaction mixture was diluted with 1N HCl (250 mL) and washed with $CH_2Cl_2$(2×80 mL). The combined organic layers were back-extracted with 1N HCl (60 mL). The combined aqueous HCl layers were cooled in an ice-bath to 2° C., and conc. (37%) HCL (30 mL) was added over 5 minutes. The desired product (bis HCl salt) began to precipitate within 30 minutes. The slurry was stirred 3 hours at 2°–5° C., then the product (bis HCl salt) was collected by filtration and dried in a vacuum oven at 55°–60° C. Yield 11.4 g (68%).

Second crop recovery

The HCl mother liquors were stirred with ethyl acetate (190 mL) and neutralized to pH 9–10 with aqueous $K_2CO_3$ (200–300 g of 25% w/w $K_2CO_3$ was required). The ethyl acetate layer was concentrated under vacuum to an oil which was redissolved in 1N HCl (90 mL) and washed with methylene chloride (45 mL). The aqueous layer was cooled to 2° C. Conc. (37%) HCl (9.0 mL) was added to precipitate a second crop. After stirring for 1–3 hours at 2°–5° C., the solid was collected by filtration and dried in a vacuum oven at 55°–60° C. Yield 2.1 g (12.6%).

Neutralization of Bis HCl Salt

The bis HCl salt (10.66 g, 21.4 mmol, mixture of first and second crops) was stirred with $CH_2Cl_2$ (110 mL) and 5% aqueous $NaHCO_3$(110 mL) until all solids dissolved (2 hours). The aqueous layer was separated and extracted with another 50 mL $CH_2Cl_2$. The combined organic extracts were dried with $Na_2SO_4$ (10 g), filtered and concentrated under vacuum at <40° C. to an oil. The oil was dried on a vacuum pump to give the title compound as a yellow foam, 9.1 g (100%).

Alternative B

The product of EXAMPLE 17 F (15.0 g, 0.053 mole) was dissolved in DMF (75 mL). Triisopropylborate (24.4 mL, 0.105 mole) was added and stirred at ambient temperature for approximately 1.5 hours. The solution was cooled to –10° C. and a solution of 5-(p-nitorphenyloxycarbony-loxymethyl)thiazole (15.0 g, 0.054 mole) in DMF (75 mL) was added over 80 minutes. The reaction was stirred for approximately 1 hour at –10° C., then was diluted with methylene chloride (250 mL) and quenched with a mixture of triethanolamine (24.8 g) and 5% aqueous sodium bicarbonate (300 mL). The biphasic mixture was stirred for 1 hour, then the layers were separated and the aqueous was extracted with another portion of methylene chloride (50 mL). The combined organic layers were extracted with 1N HCl (1×390 mL, then 1×95 mL). The acid layers were combined, cooled in an ice-bath, and further acidified with conc. HCl (50 mL) which produced a white slurry of product. The slurry was stirred for approximately 1 hour at 2° C. The desired product bis HCl salt) was collected by filtration and dried at 55° C. in a vacuum oven. Yield 18.5 g (70%).

EXAMPLE 22

Alternative Preparation of (2S,3S,5S)-5-(N-(N-((N-Methyl-N-((2-isopropyl-4-thiazolyl)methyl)amino)carbonyl)valinyl)amino)-2-(N-((5-thiazolyl)methoxycarbonyl)amino)-1,6-diphenyl-3-hydroxyhexane To a solution of the product of Example 21(9.1 g, 21.4 mmol), HOBT (3.6 g, 23.5 mmol) and N-((N-Methyl-N-((2-isopropyl-4-thiazolyl)methyl) amino)-carbonyl)-L-valine (7.37 g, 23.5 mmol)in THF (170 mL) was added DCC (4.85 g, 23.5 mmol). The solution was stirred at ambient temperature for 16 hours (DCU precipitates). THF was removed under vacuum and the resulting paste was stirred with cold 1N HCl (106 mL at 5° C.) for 3 hours to dissolve the the crude product. The DCU was removed by filtration and the filter cake was washed with 1N HCl (30 mL). $KH_2PO_4$(3.2 g) was dissolved in the combined HCl filtrates. The solution was mixed with ethyl acetate (80 mL) and neutralized to pH 7 with aqueous NaOH (60.3 g of 10% w/w NaOH). The aqueous layer was extracted with another 25 mL ethyl acetate and the combined ethyl acetate extracts were washed with aqueous $NaHOC_3$ (2×37 mL of 5% w/w $NaHOC_3$). The organic layer was dried with $Na_2SO_4$(13 g), filtered, and concentrated under vacuum at <45° C. The residue was dissolved in a 1:1 ethyl acetate/heptane mixture (200 mL) at 70° C. The solution was allowed to cool slowly and stirred overnight at room temperature to provide a thick slurry. The product was collected by filtration and washed with 1:1 ethyl acetate/heptane (20 mL). The product was dried briefly at 55° C. in a vacuum oven to obtain an approximate weight prior to the second crystallization (12.85 g, 83%). A second crystallization from 144 mL of 2:1 ethyl acetate/heptane (dissolved at ~70° C., then stirred at room temperature 12 hours) produced a thick slurry of fine white solid. The product was collected by filtration and washed with 15 mL 2:1 ethyl acetate/heptane, then dried in a vacuum oven at 55° C. for 2 days to give the desired product. Yield 11.9 g (77%).

EXAMPLE 23

Alternate Preparation of ((5-Thiazolyl)methyl)-(4-nitrophenyl)carbonate

EXAMPLE 23A

2-Amino-5-(ethoxycarbonyl)thiazole Hydrochloride

To a –10° C. solution of potassium tert-butoxide (110 g, 0.98 mol) in THF (1.9L) was added a solution of ethyl chloroacetate (100 mL, 0.934 mol) and ethyl formate (75 mL, 0.928 mol) in THF (400 mL) dropwise over 2 hours, with good mechanical stirring. The thick solution was stirred another 2 hours at ca. −1° C. then the reaction was quenched by addition of a solution of NaCl (150 g) in 1N HCL (750 mL). The mixture was allowed to warm to 20° C. and the lower aqueous layer (containing some precipitated salt) was separated. The organic layer was stripped under vacuum on a rotary evaporator. The oil was redissolved in 500 mL ethyl acetate, dried with 75 g $Na_2SO_4$ for 1 hour, filtered and concentrated under vacuum (40°–50° C. bath temperature) to an oil. The resulting crude chloroaldehyde (161 g) and thiourea (70 g, 0.92 mol) were dissolved in THF (2L) and warmed to gentle reflux (60° C.). The thiourea dissolved during warming, and within 20 minutes, product precipitated from solution. After 100 minutes the suspension was allowed to cool to room temperature, then was cooled in an ice-bath for 1 hour. The product was collected on a fritted Buchner funnel and washed with 2×100 mL cold THF, then dried overnight in a vacuum oven at 50° C. Yield: 122 g of title compound as a tan-colored solid, m.p. 182°–185° C. (dec.). $^1$H NMR (DMSO-d6) δ 7.86 (s, 1H), 4.19 (q, 2H), 1.21 (t, 3H). $^{13}$C NMR (DMSO-$d_6$) δ 171.9, 160.4, 140.4, 114.4, 61.1, 14.2.

EXAMPLE 23B

2-Amino-5-(ethoxycarbonyl)thiazole

To a −10° C. solution of potassium tert-butoxide (150 g, 1.3 mol) in THF (1.35L) was added a solution of ethyl chloroacetate (139 mL, 1.3 mol) and ethyl formate (103 mL, 1.27 mol) in THF (150 mL) dropwise over 75 minutes, with good mechanical stirring. A THF rinse (25 mL) was added over 5 minutes. The thick solution was stirred another 3 hours at ca. −5 to 0° C., then the reaction was quenched by addition of a solution of NaCl (240 g) and conc. HCl (90 mL) in water (960 mL). The mixture was allowed to warm to 15° C. and the lower aqueous layer was discarded. Thiourea (97 g, 1.27 mol) was dissolved in the crude THF solution of chloroaldehyde. The solution was warmed to 65° C. and refluxed for 1 hour, then cooled to 30° C. Addition of a solution of $K_2CO_3$ (88 g, 0.64 mol) in 1500 mL water produced two layers (aqueous pH=7). The THF was removed under vacuum at <45° C., causing the product to precipitate as a yellow solid. The slurry was cooled to 15° C., and the product was collected on a fritted Buchner funnel and washed with 3×200 mL water, then dried 24 hours in a vacuum oven at 55° C. to provide 151 g of title compound as a yellow solid, m.p. 155°–158° C. $^1$H NMR (DMSO-$d_6$) δ 7.8(br s, 2H, $NH_2$), 7.62(s, 1H), 4.13 (q, 2H), 1.18(t, 3H). $^{13}$C NMR (DMSO-$d_6$) 8 173.4, 161.3, 147.9, 114.5, 60.1, 14.3.

EXAMPLE 23C 5-(Ethoxycarbonyl)thiazole

A solution of 2-amino-5-(ethoxycarbonyl)thiazole (50 g, 0.29 mmol) in a mixture of DMF (83 mL) and THF (31 7 mL) was added dropwise over 87 minutes to a stirred 41° C. solution of isoamyl nitrite (59 mL, 0.44 mol) in DMF (130 mL). A maximum temperature of 60° C. was observed during the exothermic addition. After another 40 minutes the THF was removed under vacuum at 45° C. The concentrated DMF solution was cooled to 25° C. and diluted with toluene (420 mL) and water (440 mL). The toluene layer was extracted with 3×120 mL water, then dried with $Na_2SO_4$ (50 g) for 1 hour. After filtration the toluene layer was stripped on a rotary evaporator at 50° C. bath temperature, then on a vacuum pump at 21° C. The crude residue containing the title compound weighed 65.6 g. This material was used directly in the next step. A sample of similarly prepared material was purified by column chromatography to give a yellow oil. $_1$H NMR ($CDCl_3$) δ 8.95(s, 1H), 8.51(s, 1H), 4.39 (q, 2H), 1.40 (t, 3H). $^{13}$C NMR ($CDCl_3$) δ 161.0, 157.9, 148.6, 129.8, 61,6, 14.1.

EXAMPLE 23D 5-(Hydroxymethyl)thiazole

To a slurry of lithium aluminum hydride (9.0 g) in THF (633 mL) was added a solution of crude 5-(ethoxycarbonyl)thiazole (65.6 g from Example 37C) in THF (540 mL) over 95 minutes at 0°–5° C. After an additional 25 minutes, the reaction was quenched at 5° C. by sequential addition of water (8.1 mL), 15% NaOH (8.1 mL), and water (24.3 mL). After drying with $Na_2SO_4$(44 g) for 2 hours, the slurry was filtered, and the filter cake was washed with 100 mL THF. The combined filtrates were concentrated under vacuum at 45° C. to a brown oil (39 g). The oil was fractionally distilled through a short-path apparatus. The product fractions distilled at 97°–104° C. vapor temperature at 3°–5mm, providing 20.5 g of the title compound as a turbid orange oil. $_1$H NMR ($CDCl_3$) δ 8.74(s, 1H), 7.72(s, 1H), 140.0, 139.5, 56.6.

EXAMPLE 23E 5-(p-Nitrophenyoxycarbonyloxymethyl)thiazole Hydrochloride

Distilled 5-(hydroxymethyl)thiazole (14.1 g, 123 mmol) and triethylamine (17.9 mL, 129 mmol) were dissolved in ethyl acetate (141 mL) and cooled to −1° C. (ice/salt bath). A solution of 4-nitrophenyl chloroformate (26.0 g, 129mmol) dissolved in ethyl acetate (106 mL) was added dropwise over 50 minutes at an internal temperature of 0°–4° C. An ethyl acetate flask rinse (20 mL) was also added. Salts precipitated from solution throughout the addition. The yellow mixture was stirred another 1 hour 45 minutes at 0°–2° C., then a solution of dilute HCl (3.1 g, 31 mmol of conc. HCl in 103 mL water) was added at once. The mixture was stirred for 0.5 hours while warming to 15° C., then stirring was stopped. The organic layer was washed twice with aqueous 5% $K_2CO_3$ solution (2×70 mL), then dried with $Na_2SO_4$(30 g). After filtration the solution was concentrated under vacuum on a rotary evaporater (bath temperature of 41° C.) to a brown oil (38 g). The crude 5-(p-nitrophenyoxycarbonyloxymethyl)-thiazole was dissolved in ethyl acetate (282 mL), then cooled in an ice bath to 2° C. Dry HCl gas (7.1 g, 195 mmol) was bubbled in slowly over 50 minutes (temperature 2°–4° C.). After stirring for another 1 hour 45 minutes at 2°–4° C., the solid precipitate was collected on a sintered glass funnel under a nitrogen blanket and the flask was washed out with 50 mL cold ethyl acetate which was used to rinse the filter cake. The cake was dried on the funnel under strong nitrogen purge for 15 minutes then dried in a vacuum oven at 50° C. with a nitrogen purge to provide 29.05 g of the title compound as tan powder, m.p. 31°–135° C. (dec.). $^1$H NMR (DMSO-d6) δ 9.21 (d, 1H), 8.27 (m, 2H), 8.06(d, 1H), 7.52 (m, 2H), 5.54 (s, 2H). $^{13}$C NMR (DMSO-d6) δ 5 157.3, 155.2, 151.8, 45.3, 143.7, 131.9, 125.5, 122.7, 62.1.

EXAMPLE 23F 5-(D-Nitrophenyoxycarbonyloxymethyl)thiazole 5-(p-Nitrophenoxycarbonyloxymethyl)thiazole hydrochloride (3.0 g) was slurried in ethyl acetate (30 mL) and cooled to 10°–15° C. A solution of 5% aqueous potassium carbonate (30 mL) was added with rapid stirring. After 15 minutes, stirring was stopped and the aqueous layer was separated. The organic layer was dried with $Na_2SO_4$ (3 g), filtered, and solvent was distilled under vacuum to give 2.49 g of the title compound as a brown syrup which slowly solidified, m.p. 62°–64° C. 1H NMR ($CDCl_3$) δ 8.90 (d, 1H), 8.29 (m, 2H), 8.01 (d, 1H), 7.39 (m, 2H), 5.52 (s, 2H). $^{13}$C NMR ($CDCl_{13}$) δ 155.4, 155.2, 152.2, 145.4, 144.9, 130.6, 125.3, 121.6, 61.9.

EXAMPLE 24

Alternative Preparation of N-((N-Methyl-N-((2-isopropyl-4-thiazolyl)methyl)amino)carbonyl)-L-valine

EXAMPLE 24A

Thioisobutyramide

To a 1 liter three neck round bottom flask equipped with mechanical stirrer, nitrogen atmosphere, condensor, thermocouple and 15° C. water bath was charged (26.0 g, 0.298 mols) isobutyramide followed by (19.9 g, 0.045 mols) phosphorous pentasulfide and 375 mls THF. This solution was stirred at 20°±5° C. for 3 hours, then was warmed to 60° C. and stirred an additional 3 hours. The THF was removed under vacuum with a 50° C. bath temperature to afford a yellow oil. This oil was neutralized with a solution of 5 g NaOH, 10 g NaCl and 90 g water. Next the product was extracted into EtOAc (2×250 mls) and the combined organics reduced under vacuum to an oil. The oil was dissolved in 50 mls THF and again the solvent was removed under vacuum to give the desired product as a yellow oil. (yield approx. 27 grams, 88%).

EXAMPLE 24B

2-Isopropyl-4-(((N-methyl)amino)methyl)thiazole

The thioisobutyramide resulting from Example 24A was dissolved in 70mls THF and added slowly to a solution of (34.1 g, .27 mols) 1,3-dichloracetone in 40 mls THF. A 10 ml rinse of THF was used to completely transfer the thioamide. The reaction wass carried out in a 250 ml flask with mechanical stirring under nitrogen atmosphere. The reaction temperature was maintained below 25° C. during addition with a 15°±5° C. bath. The bath was kept in place for 1 hour after which it was removed and the reaction stirred for 18 hours. Next this stirred chloromethyl-thiazole solution was added to 376 mls (4.37 mols) 40% aqueous methylamine solution at 15° C. in a 1 liter flask. The temperature was maintained below 25° C. during addition. After half an hour the bath was removed and the reaction stirred for 3 hours at ambient temperature. The solvent was removed under vacuum with a 50° C. bath to an end volume of 310mls. The residue was then basified with 50 g 10% NaOH to pH 12 and extracted into methylene chloride (2×160 mls). The combined organics were then washed with 1×150 g of 20% ammonium chloride followed by 1×90 g of 20% ammonium chloride. The combined aqueous washes were then back extracted with 150 mls methylene chloride. The combined product methylene chloride layers were then extracted with 100 g of a solution of 25 g conc. HCl and 75 g water. This acidic product solution was then washed with 135 mls methylene chloride. Next the acidic product solution was cooled, then neutralized with 100 g 20% NaOH solution. The product was extracted from this mixture with methylene chloride (2×135 mls). The solvent was removed under vacuum to afford the desired product as an amber oil. (yield approx. 28 grams)

EXAMPLE 24C

N-((N-Methyl-N-((2-isopropyl-4-thiazolyl)methyl)amino)carbonyl)-L-valine Methyl Ester Into a 500 ml 3-neck round bottom flask equipped with mechanical stirrer, nitrogen atmosphere, thermocouple, heating mantle and condensor was charged the product of EXAMPLE 24 B (28.1 g, .165 mols), phenoxycarbonyl-(L)-valine (41.5 g, .165 mol) and 155 ml toluene. This solution was warmed to reflux (110° C.) and stirred for three hours, then cooled to 20°±5° C. and washed with 2×69 ml 10% citric acid followed by 1×69 ml water, 1×116 mls 4% sodium hydroxide, 1×58 ml 4% sodium hydroxide and finally 1×58 ml water. The organic product solution was then treated with 3 grams of activated carbon at reflux for 15 minutes, filtered through infusorial earth to remove carbon, and the carbon/infusorial earth cake was washed with 25 ml hot toluene. Next the solvent was removed to afford a brown oil which solidified upon cooling. This brown solid was dissolved with warming in 31 ml EtOAc and 257 ml heptane at 60°±5° C. This solution was slowly cooled to 25° C., stirred 12 hours, cooled further to 0° C., and stirred 3 hours. The crystals were collected by filtration and washed with 50 ml 1:9 EtOAc/Heptane. The solid was dried in a 50° C. vacuum oven for 12 hours to afford 41.5 grams of the desired product as a tan-colored solid (76.9%).

EXAMPLE 24D

N-((N-Methyl-N-((2-isopropyl-4-thiazolyl)methyl)amino)carbonyl)-L-valine

To a one liter three neck flask was charged the product of Example 24C (50 g, 0.153 mol), lithium hydroxide monohydrate (13 g, 0.310 mol), 200 ml THF and 190 ml water. This hazy solution was stirred for 2 hours. The reaction was quenched with a solution of conc. HCl (32.4 g, 0.329 mol) in 65 mL water, the THF was removed under vacuum and the product extracted into methylene chloride (3×210 ml). (NOTE: If necessary, the pH of the aqueous layer should be adjusted to maintain pH 1–4 during the extractions.) The combined organics were then dried with 50 g sodium sulfate, filtered with a 150 ml methylene chloride rinse of the sodium sulfate, and the solvent was removed under vacuum. The product was dissolved in 450 ml THF and again the solvent was removed. Next the product was dissolved in 475 ml THF containing 0.12 g butylated hydroxytoluene (BHT) for storage. If desired, the solvent can be removed under vacuum and the residual syrup dried in a vacuum oven at 55° C. to provide a glassy solid.

The above process for the preparation of compound III is disclosed in PCT Patent Application No. WO94/14436, published Jul. 7, 1994, which is hereby incorporated herein by reference.

Protocol For Oral Bioavailability Studies

Dogs (beagle dogs, mixed sexes, weighing 7–14 kg) were fasted overnight prior to dosing, but were permitted water ad libitum. Each dog received a 0.5 mg/kg subcutaneous dose of histamine approximately 30 minutes prior to dosing. Each dog received a single solid dosage form corresponding to a 5mg/kg dose of the drug. The dose was followed by approximately 10 milliliters of water. Blood samples were obtained from each animal prior to dosing and 0.25, 0.5, 1.0, 1.5, 2, 3, 4, 6, 8, 10 and 12 hours after drug administration. The plasma was separated from the red cells by centrifugation and frozen (−30° C.) until analysis. Concentrations of parent drug were determined by reverse phase HPLC with low wavelength UV detection following liquid-liquid extraction of the plasma samples. The parent drug area under the curve was calculated by the trapezoidal method over the time course of the study. The absolute bioavailability of each test composition was calculated by comparing the area under the curve after oral dosing to that obtained from a single intravenous dose. Each capsule or capsule composition was evaluated in a group containing at least six dogs; the values reported are averages for each group of dogs. The average bioavailability data for the compositions of the Examples is shown in Table 1.

TABLE 1

| Example No. | Mean % Bioavailability |
| --- | --- |
| Example 1 | <2.0 |
| Example 2 | <2.0 |
| Example 3 | 2.5 |
| Example 4 | 4.2 |
| Example 5 | 2.2 |
| Example 6 | 1.3 |
| Example 7 | 71.7 |
| Example 8 | 48.1 |
| Example 9 | 66.5 |
| Example 10 | 65.3 |
| Example 11 | 51.7 |
| Example 12 | 34.8 |
| Example 14 | 53.5 |
| Example 15 | 89.6 |
| Example 16 | 34.4 |

This data indicates that the solid composition of the invention provides significantly better oral bioavailability than non-formulated compound III or non-formulated salts of compound III. This data also indicates that the solid composition of the invention provides significantly better oral bioavailability than a PEG melt comprising compound III or a standard solid composition (tablet or capsule) comprising compound III and a surfactant and an acid.

Compounds I, II and III are inhibitors of HIV-1 and HIV-2 protease. They are useful for inhibiting an HIV infection and treating AIDS in humans. Total daily dose of compound I, II or III administered to a human in single or divided doses may be in amounts, for example, from 0.001 to 1000 mg/kg body weight daily but more usually 0.1 to 50 mg/kg body weight daily. Dosage unit compositions may contain such amounts of submultiples thereof to make up the daily dose. It will be understood, however, that the specific dose level for any particular patient will depend upon a variety of factors including the age, body weight, general health, sex, diet, time of administration, rate of excretion, drugs administered in combination and the severity of the particular disease undergoing therapy.

The foregoing is merely illustrative of the invention and is not intended to limit the invention to the disclosed compounds, methods and compositions. Variations and changes which are obvious to one skilled in the art are intended to be within the scope and nature of the invention which are defined in the appended claims.

What is claimed is:

1. A solid pharmaceutical composition comprising a pharmaceutically acceptable adsorbent or a mixture of pharmaceutically acceptable adsorbents to which is adsorbed a mixture of (1) a pharmaceutically acceptable organic solvent or a mixture of pharmaceutically acceptable organic solvents, (2) an HIV protease inhibiting compound selected from the group consisting of:

N-(2(R)-hydroxy-1(S)-indanyl)-2(R)-phenylmethyl-4(S)-hydroxy-5-(1-(4-(3-pyridylmethyl)-2(S)-N'-(t-butylcarboxamido)-piperazinyl))-pentaneamide;

N-tert-butyl-decahydro-2-(2(R)-hydroxy-4-phenyl-3(S)-((N-(2-quinolylcarbonyl)-L-asparaginyl) amino)butyl)-(4aS,8aS)-isoqulnoline-3(S)-carboxamide;

5(S)-Boc-amino-4(S)-hydroxy-6-phenyl-2(R)-phenylmethylhexanovl-(L)-Val-(L)-Phe-morpholin-4-ylamide;

1-Naphthoxyacetyl-beta-methylthio-Ala-(2S,3S)-3-amino-2-hydroxy-4-butanoyl-1,3-thiazolidine-4-t-butylamide;

(1S-(1R*(R*), 2S*)}-$N^1$(3-((((1.1-dimethylethyl)amino)carbonyl)(2-methylpropyl)amino)-2 hydroxy-1-(phenylmethyl) propyl)-2-((2-quinolinylcarbonyl)amino)-butanediamide;

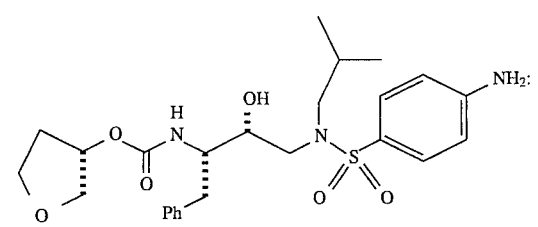

and

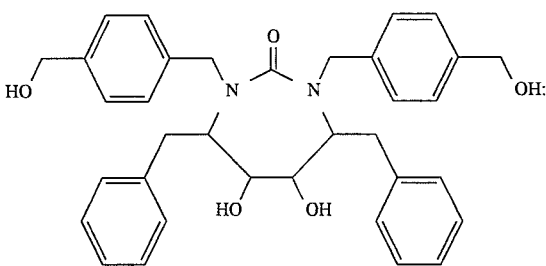

or a pharmaceutically acceptable salt thereof;
and (3) a pharmaceutically acceptable acid or a combination of pharmaceutically acceptable acids.

2. The composition of claim 1 wherein the composition is encapsulated in a hard gelatin capsule.

3. The composition of claim 1 wherein the adsorbed mixture further comprises one or more additives independently selected from pharmaceutically acceptable oils, pharmaceutically acceptable surfactants and antioxidants.

* * * * *